United States Patent
Dann et al.

(10) Patent No.: US 7,846,138 B2
(45) Date of Patent: Dec. 7, 2010

(54) CUFF AND SLEEVE SYSTEM FOR GASTROINTESTINAL BYPASS

(75) Inventors: Mitchell Dann, Wilson, WY (US); Jonathan Kagan, Hopkins, MN (US); Paul Swain, London (GB); Joshua Butters, Chandler, AZ (US); Lee Guterman, Amherst, NY (US)

(73) Assignee: ValenTx, Inc., Carpinteria, CA (US)

( * ) Notice: Subject to any disclaimer, the term of this patent is extended or adjusted under 35 U.S.C. 154(b) by 1099 days.

(21) Appl. No.: 11/430,274

(22) Filed: May 8, 2006

(65) Prior Publication Data

US 2006/0293742 A1    Dec. 28, 2006

Related U.S. Application Data

(63) Continuation of application No. 11/400,724, filed on Apr. 7, 2006, which is a continuation-in-part of application No. 11/124,634, filed on May 5, 2005, and a continuation-in-part of application No. 10/698,148, filed on Oct. 31, 2003, said application No. 11/124,634 is a continuation-in-part of application No. 10/998,424, filed on Nov. 29, 2004, and a continuation-in-part of application No. 11/025,364, filed on Dec. 29, 2004.

(60) Provisional application No. 60/569,442, filed on May 7, 2004, provisional application No. 60/613,917, filed on Sep. 27, 2004, provisional application No. 60/480,485, filed on Jun. 21, 2003, provisional application No. 60/448,817, filed on Feb. 21, 2003, provisional application No. 60/437,513, filed on Dec. 30, 2002, provisional application No. 60/430,857, filed on Dec. 3, 2002, provisional application No. 60/428,483, filed on Nov. 22, 2002, provisional application No. 60/422,987, filed on Nov. 1, 2002.

(51) Int. Cl.
*A61M 5/00* (2006.01)

(52) U.S. Cl. .................. 604/263; 604/264; 604/271

(58) Field of Classification Search ................. 604/263, 604/264, 270, 500, 523, 275–279; 606/153; 623/23.64–23.7
See application file for complete search history.

(56) References Cited

U.S. PATENT DOCUMENTS 3,357,432 A    12/1967 Sparks (Continued)

FOREIGN PATENT DOCUMENTS

EP    0817598    2/1996

(Continued)

OTHER PUBLICATIONS

PCT International Search Report for PCT/US2005/15795 mailed Nov. 14, 2005.

(Continued)

*Primary Examiner*—Kevin C Sirmons
*Assistant Examiner*—Phillip Gray
(74) *Attorney, Agent, or Firm*—Knobbe, Martens, Olson & Bear LLP

(57) ABSTRACT

The present invention provides devices and methods for attachment of an endolumenal gastrointestinal device, such as an artificial stoma device, a gastrointestinal bypass sleeve or other therapeutic or diagnostic device, within a patient's digestive tract. In one application of the invention, an endolumenal bypass sleeve is removeably attached in the vicinity of the gastroesophageal junction to treat obesity and/or its comorbidities, such as diabetes. The bypass sleeve may be at least partially deployed by eversion.

13 Claims, 12 Drawing Sheets

U.S. PATENT DOCUMENTS

| | | | |
|---|---|---|---|
| 3,589,356 A | 6/1971 | Silverman | |
| 3,982,544 A | 9/1976 | Dyck | |
| 4,006,747 A | 2/1977 | Kronenthal et al. | |
| 4,043,345 A | 8/1977 | Kramann et al. | |
| 4,109,659 A | 8/1978 | Sheridan | |
| 4,134,405 A | 1/1979 | Smit | |
| 4,217,664 A | 8/1980 | Faso | |
| 4,235,238 A | 11/1980 | Ogiu et al. | |
| 4,252,131 A | 2/1981 | Hon et al. | |
| 4,271,839 A | 6/1981 | Fogarty et al. | |
| 4,315,509 A | 2/1982 | Smit | |
| 4,329,995 A | 5/1982 | Anthracite | |
| 4,501,264 A | 2/1985 | Rockey | |
| 4,532,926 A | 8/1985 | O'Holla | |
| 4,606,347 A | 8/1986 | Fogarty et al. | |
| 4,630,609 A | 12/1986 | Chin | |
| 4,641,653 A | 2/1987 | Rockey | |
| 4,719,916 A * | 1/1988 | Ravo | 606/156 |
| 4,763,653 A | 8/1988 | Rockey | |
| 4,846,836 A | 7/1989 | Reich | |
| 4,863,440 A | 9/1989 | Chin | |
| 4,946,440 A | 8/1990 | Hall | |
| 5,085,661 A | 2/1992 | Moss | |
| RE34,021 E | 8/1992 | Mueller et al. | |
| 5,171,305 A | 12/1992 | Schickling et al. | |
| 5,236,423 A | 8/1993 | Mix et al. | |
| 5,306,300 A | 4/1994 | Berry | |
| 5,314,473 A | 5/1994 | Godin | |
| 5,411,508 A | 5/1995 | Bessler et al. | |
| 5,431,666 A | 7/1995 | Sauer et al. | |
| 5,458,573 A | 10/1995 | Summers | |
| 5,470,337 A | 11/1995 | Moss | |
| 5,582,616 A | 12/1996 | Bolduc et al. | |
| 5,645,568 A | 7/1997 | Chervitz et al. | |
| 5,785,684 A | 7/1998 | Zimmon | |
| 5,820,584 A | 10/1998 | Crabb | |
| 5,824,008 A | 10/1998 | Bolduc et al. | |
| 5,843,164 A | 12/1998 | Frantzen | |
| 5,861,036 A | 1/1999 | Godin | |
| 5,887,594 A | 3/1999 | LoCicero, III | |
| 5,957,940 A | 9/1999 | Tanner et al. | |
| 5,972,023 A | 10/1999 | Tanner et al. | |
| 5,997,556 A | 12/1999 | Tanner | |
| 6,113,609 A | 9/2000 | Adams | |
| 6,193,733 B1 | 2/2001 | Adams | |
| 6,254,642 B1 * | 7/2001 | Taylor | 623/23.64 |
| 6,264,700 B1 | 7/2001 | Kilcoyne et al. | |
| 6,285,897 B1 | 9/2001 | Kilcoyne et al. | |
| 6,312,437 B1 | 11/2001 | Kortenbach | |
| 6,338,345 B1 | 1/2002 | Johnson et al. | |
| 6,387,104 B1 | 5/2002 | Pugsley, Jr. et al. | |
| 6,409,656 B1 | 6/2002 | Sangouard et al. | |
| 6,447,533 B1 | 9/2002 | Adams | |
| 6,494,888 B1 | 12/2002 | Laufer et al. | |
| 6,520,974 B2 | 2/2003 | Tanner et al. | |
| 6,535,764 B2 | 3/2003 | Imran et al. | |
| 6,544,291 B2 | 4/2003 | Taylor | |
| 6,558,400 B2 | 5/2003 | Deem et al. | |
| 6,558,429 B2 | 5/2003 | Taylor | |
| 6,592,596 B1 | 7/2003 | Geitz | |
| 6,595,911 B2 | 7/2003 | LoVuolo | |
| 6,626,916 B1 | 9/2003 | Yeung et al. | |
| 6,626,919 B1 | 9/2003 | Swanstrom | |
| 6,675,809 B2 | 1/2004 | Stack et al. | |
| 6,699,263 B2 | 3/2004 | Cope | |
| 6,702,735 B2 | 3/2004 | Kelly | |
| 6,736,828 B1 | 5/2004 | Adams et al. | |
| 6,740,121 B2 | 5/2004 | Geitz | |
| 6,746,489 B2 | 6/2004 | Dua et al. | |
| 6,764,518 B2 | 7/2004 | Godin | |
| 6,790,237 B2 | 9/2004 | Stinson | |
| 6,845,776 B2 | 1/2005 | Stack et al. | |
| 7,037,344 B2 | 5/2006 | Kagan et al. | |
| 7,120,498 B2 | 10/2006 | Imran et al. | |
| 7,121,283 B2 | 10/2006 | Stack et al. | |
| 7,152,607 B2 | 12/2006 | Stack et al. | |
| 7,175,669 B2 | 2/2007 | Geitz | |
| RE39,533 E | 3/2007 | Ranoux | |
| 7,220,284 B2 | 5/2007 | Kagan et al. | |
| 7,244,270 B2 | 7/2007 | Lesh | |
| 7,267,694 B2 | 9/2007 | Levine et al. | |
| 7,288,099 B2 | 10/2007 | Deem et al. | |
| 7,306,614 B2 | 12/2007 | Weller et al. | |
| 7,309,341 B2 | 12/2007 | Ortiz et al. | |
| 7,314,489 B2 | 1/2008 | McKenna et al. | |
| 7,329,285 B2 | 2/2008 | Levine et al. | |
| 7,347,875 B2 | 3/2008 | Levine et al. | |
| 7,354,454 B2 | 4/2008 | Stack et al. | |
| 7,371,215 B2 | 5/2008 | Colliou et al. | |
| 7,483,754 B2 | 1/2009 | Imran et al. | |
| 7,509,175 B2 | 3/2009 | Sparks et al. | |
| 7,520,884 B2 | 4/2009 | Swanstrom et al. | |
| 2001/0016748 A1 | 8/2001 | Tanner et al. | |
| 2001/0020189 A1 | 9/2001 | Taylor | |
| 2001/0020190 A1 | 9/2001 | Taylor | |
| 2001/0044595 A1 | 11/2001 | Reydel et al. | |
| 2001/0056282 A1 | 12/2001 | Sonnenschein et al. | |
| 2002/0016607 A1 | 2/2002 | Bonadio et al. | |
| 2002/0026214 A1 | 2/2002 | Tanner et al. | |
| 2002/0035370 A1 | 3/2002 | Kortenbach | |
| 2002/0040226 A1 | 4/2002 | Laufer et al. | |
| 2002/0058960 A1 | 5/2002 | Hudson et al. | |
| 2002/0082621 A1 | 6/2002 | Schurr et al. | |
| 2002/0165589 A1 | 11/2002 | Imaran et al. | |
| 2002/0183768 A1 | 12/2002 | Deem et al. | |
| 2002/0188354 A1 | 12/2002 | Peghini | |
| 2003/0014064 A1 | 1/2003 | Blatter | |
| 2003/0018358 A1 | 1/2003 | Saadat | |
| 2003/0040804 A1 | 2/2003 | Stack et al. | |
| 2003/0040808 A1 | 2/2003 | Stack et al. | |
| 2003/0055313 A1 | 3/2003 | Anderson et al. | |
| 2003/0055442 A1 | 3/2003 | Laufer et al. | |
| 2003/0065340 A1 | 4/2003 | Geitz | |
| 2003/0065359 A1 | 4/2003 | Weller et al. | |
| 2003/0093117 A1 | 5/2003 | Saadat | |
| 2003/0109892 A1 | 6/2003 | Deem et al. | |
| 2003/0109931 A1 | 6/2003 | Geitz | |
| 2003/0120285 A1 | 6/2003 | Kortenbach | |
| 2003/0130560 A1 | 7/2003 | Suzuki et al. | |
| 2003/0130561 A1 | 7/2003 | Suzuki et al. | |
| 2003/0139752 A1 | 7/2003 | Pasricha et al. | |
| 2003/0171775 A1 | 9/2003 | Belson | |
| 2003/0181929 A1 | 9/2003 | Geitz | |
| 2003/0191497 A1 | 10/2003 | Cope | |
| 2003/0199989 A1 | 10/2003 | Stack et al. | |
| 2003/0199990 A1 | 10/2003 | Stack et al. | |
| 2003/0199991 A1 | 10/2003 | Stack et al. | |
| 2003/0208209 A1 | 11/2003 | Gambale et al. | |
| 2004/0002734 A1 | 1/2004 | Fallin et al. | |
| 2004/0024427 A1 | 2/2004 | Imran et al. | |
| 2004/0039452 A1 | 2/2004 | Bessler | |
| 2004/0044364 A1 | 3/2004 | DeVries et al. | |
| 2004/0059349 A1 | 3/2004 | Sixto, Jr. et al. | |
| 2004/0059354 A1 | 3/2004 | Smith | |
| 2004/0082963 A1 | 4/2004 | Gannoe et al. | |
| 2004/0087976 A1 | 5/2004 | DeVries et al. | |
| 2004/0087977 A1 | 5/2004 | Nolan et al. | |
| 2004/0089313 A1 | 5/2004 | Utley et al. | |
| 2004/0092892 A1 | 5/2004 | Kagan et al. | |
| 2004/0092974 A1 | 5/2004 | Gannoe et al. | |
| 2004/0093065 A1 | 5/2004 | Yachia et al. | |
| 2004/0097986 A1 | 5/2004 | Adams | |
| 2004/0097987 A1 | 5/2004 | Pugsley et al. | |
| 2004/0102855 A1 | 5/2004 | Shank | |

| | | | | | | |
|---|---|---|---|---|---|---|
| 2004/0107004 A1 | 6/2004 | Levine et al. | | 2006/0047289 A1 | 3/2006 | Fogel |
| 2004/0116949 A1 | 6/2004 | Ewers et al. | | 2006/0064120 A1 | 3/2006 | Levine et al. |
| 2004/0117031 A1 | 6/2004 | Stack et al. | | 2006/0074458 A1 | 4/2006 | Imran |
| 2004/0122453 A1 | 6/2004 | Deem et al. | | 2006/0155312 A1 | 7/2006 | Levine et al. |
| 2004/0122456 A1 | 6/2004 | Saadat et al. | | 2006/0161139 A1 | 7/2006 | Levine et al. |
| 2004/0122473 A1 | 6/2004 | Ewers et al. | | 2006/0161172 A1 | 7/2006 | Levine et al. |
| 2004/0133089 A1 | 7/2004 | Kilcoyne et al. | | 2006/0161187 A1 | 7/2006 | Levine et al. |
| 2004/0133147 A1 | 7/2004 | Woo | | 2006/0161265 A1 | 7/2006 | Levine et al. |
| 2004/0133219 A1 | 7/2004 | Forsell | | 2006/0173422 A1 | 8/2006 | Reydel et al. |
| 2004/0133238 A1 | 7/2004 | Cerier | | 2006/0206063 A1 | 9/2006 | Kagan et al. |
| 2004/0138525 A1 | 7/2004 | Saadat et al. | | 2006/0206064 A1 | 9/2006 | Kagan et al. |
| 2004/0138529 A1 | 7/2004 | Wiltshire et al. | | 2006/0235446 A1 | 10/2006 | Godin |
| 2004/0138761 A1 | 7/2004 | Stack et al. | | 2006/0265082 A1 | 11/2006 | Meade et al. |
| 2004/0143342 A1 | 7/2004 | Stack et al. | | 2006/0287734 A1 | 12/2006 | Stack et al. |
| 2004/0147958 A1 | 7/2004 | Lam et al. | | 2006/0293742 A1 | 12/2006 | Dann et al. |
| 2004/0148034 A1 | 7/2004 | Kagan et al. | | 2007/0005147 A1 | 1/2007 | Levine et al. |
| 2004/0153167 A1 | 8/2004 | Stack et al. | | 2007/0010794 A1 | 1/2007 | Dann et al. |
| 2004/0158331 A1 | 8/2004 | Stack et al. | | 2007/0010864 A1 | 1/2007 | Dann et al. |
| 2004/0162567 A9 | 8/2004 | Adams | | 2007/0010865 A1 | 1/2007 | Dann et al. |
| 2004/0162568 A1 | 8/2004 | Saadat et al. | | 2007/0010866 A1 | 1/2007 | Dann et al. |
| 2004/0167546 A1 | 8/2004 | Saadat et al. | | 2007/0016244 A1 | 1/2007 | Behl et al. |
| 2004/0181242 A1 | 9/2004 | Stack et al. | | 2007/0027548 A1 | 2/2007 | Levine et al. |
| 2004/0186514 A1 | 9/2004 | Swain et al. | | 2007/0027549 A1 | 2/2007 | Godin |
| 2004/0193190 A1 | 9/2004 | Luddicoat et al. | | 2007/0032879 A1 | 2/2007 | Levine et al. |
| 2004/0199189 A1 | 10/2004 | Gifford et al. | | 2007/0083271 A1 | 4/2007 | Levine et al. |
| 2004/0204768 A1 | 10/2004 | Geitz | | 2007/0100367 A1 | 5/2007 | Quijano et al. |
| 2004/0220682 A1 | 11/2004 | Levine et al. | | 2007/0100368 A1 | 5/2007 | Quijano et al. |
| 2004/0225183 A1 | 11/2004 | Michlitsch et al. | | 2007/0106233 A1 | 5/2007 | Huang et al. |
| 2004/0225305 A1 | 11/2004 | Ewers et al. | | 2007/0106313 A1 | 5/2007 | Golden et al. |
| 2004/0243152 A1 | 12/2004 | Taylor et al. | | 2007/0129719 A1 | 6/2007 | Kendale et al. |
| 2004/0243195 A1 | 12/2004 | Imran et al. | | 2007/0156248 A1 | 7/2007 | Marco et al. |
| 2004/0249362 A1 | 12/2004 | Levine et al. | | 2007/0208360 A1 | 9/2007 | Demarais et al. |
| 2004/0249367 A1 | 12/2004 | Saadat et al. | | 2007/0219571 A1 | 9/2007 | Balbierz et al. |
| 2005/0033240 A1 | 2/2005 | Oishi et al. | | 2007/0225555 A1 | 9/2007 | Stefanchik |
| 2005/0033331 A1 | 2/2005 | Burnett et al. | | 2007/0233162 A1 | 10/2007 | Gannoe et al. |
| 2005/0033332 A1 | 2/2005 | Burnett | | 2007/0293885 A1 | 12/2007 | Binmoeller |
| 2005/0049718 A1 | 3/2005 | Dann et al. | | 2008/0004606 A1 | 1/2008 | Swain et al. |
| 2005/0065401 A1 | 3/2005 | Saadat et al. | | 2008/0033574 A1 | 2/2008 | Bessler et al. |
| 2005/0075653 A1 | 4/2005 | Saadat et al. | | 2008/0058887 A1 | 3/2008 | Griffin et al. |
| 2005/0075654 A1 | 4/2005 | Kelleher | | 2008/0103604 A1 | 5/2008 | Levine et al. |
| 2005/0080431 A1 | 4/2005 | Levine et al. | | 2008/0167606 A1 | 7/2008 | Dann et al. |
| 2005/0080444 A1 | 4/2005 | Kraemer et al. | | 2008/0167610 A1 | 7/2008 | Dann et al. |
| 2005/0085787 A1 | 4/2005 | Laufer | | 2008/0167629 A1 | 7/2008 | Dann et al. |
| 2005/0085900 A1 | 4/2005 | Case et al. | | 2008/0208356 A1 | 8/2008 | Stack et al. |
| 2005/0085923 A1 | 4/2005 | Levine et al. | | 2008/0221597 A1 | 9/2008 | Wallace et al. |
| 2005/0096673 A1 | 5/2005 | Stack et al. | | 2008/0243071 A1 | 10/2008 | Quijano et al. |
| 2005/0096750 A1 | 5/2005 | Kagan et al. | | 2008/0249533 A1 | 10/2008 | Godin |
| 2005/0101977 A1 | 5/2005 | Gannoe et al. | | 2008/0269797 A1 | 10/2008 | Stack et al. |
| 2005/0125020 A1 | 6/2005 | Meade et al. | | 2009/0012541 A1 | 1/2009 | Dahl et al. |
| 2005/0125075 A1 | 6/2005 | Meade et al. | | 2009/0012544 A1 | 1/2009 | Thompson et al. |
| 2005/0143784 A1 | 6/2005 | Imran | | 2009/0012553 A1 | 1/2009 | Swain et al. |
| 2005/0177181 A1 | 8/2005 | Kagan et al. | | 2009/0024143 A1 | 1/2009 | Crews et al. |
| 2005/0187567 A1 | 8/2005 | Baker et al. | | | | |
| 2005/0192629 A1 | 9/2005 | Jaadat et al. | | | FOREIGN PATENT DOCUMENTS | |
| 2005/0197714 A1 | 9/2005 | Sayet | | EP | 1237501 | 9/2000 |
| 2005/0197715 A1 | 9/2005 | Kugler et al. | | WO | WO 80/00007 | 1/1980 |
| 2005/0203547 A1 | 9/2005 | Weller et al. | | WO | WO 91/01117 A1 | 2/1991 |
| 2005/0222592 A1 | 10/2005 | Gannoe et al. | | WO | WO 96/29954 A1 | 10/1996 |
| 2005/0228413 A1 | 10/2005 | Binmoeller et al. | | WO | WO 98/56440 A1 | 12/1998 |
| 2005/0228504 A1 | 10/2005 | Demerais | | WO | WO 99/60931 A1 | 12/1999 |
| 2005/0247320 A1 | 11/2005 | Stack et al. | | WO | WO 00/12027 A1 | 3/2000 |
| 2005/0256587 A1 | 11/2005 | Egan | | WO | WO 01/35834 A1 | 5/2001 |
| 2005/0261549 A1 | 11/2005 | Hewit et al. | | WO | WO 01/43663 A1 | 6/2001 |
| 2005/0261712 A1 | 11/2005 | Balbierz et al. | | WO | WO 01/85034 A1 | 11/2001 |
| 2005/0267499 A1 | 12/2005 | Stack et al. | | WO | WO 02/094132 A1 | 11/2002 |
| 2005/0267595 A1 | 12/2005 | Chen et al. | | WO | WO 02/102227 A2 | 12/2002 |
| 2006/0009858 A1 | 1/2006 | Levine et al. | | WO | WO 03/017882 A2 | 3/2003 |
| 2006/0015125 A1 | 1/2006 | Swain | | WO | WO 03/086246 A1 | 10/2003 |
| 2006/0020164 A1 | 1/2006 | Butler et al. | | WO | WO 03/086247 A1 | 10/2003 |
| 2006/0020247 A1 | 1/2006 | Kagan et al. | | WO | WO 03/094785 A1 | 11/2003 |
| 2006/0020277 A1 | 1/2006 | Gostout et al. | | WO | WO 2004/017863 A2 | 3/2004 |
| 2006/0020278 A1 | 1/2006 | Burnett et al. | | WO | WO 2004/021894 A2 | 3/2004 |
| 2006/0025819 A1 | 2/2006 | Nobis et al. | | | | |

| | | |
|---|---|---|
| WO | WO 2004/041119 A2 | 5/2004 |
| WO | WO 2004/047686 A1 | 6/2004 |
| WO | WO 2004/049982 A2 | 6/2004 |
| WO | WO 2004/064680 A1 | 8/2004 |
| WO | WO 2004/064685 A1 | 8/2004 |
| WO | WO 2004/080336 A2 | 9/2004 |
| WO | WO 2004/087014 A2 | 10/2004 |
| WO | WO 2004/087233 A2 | 10/2004 |
| WO | WO 2004/086984 A1 | 11/2004 |
| WO | WO 2004/103214 A1 | 12/2004 |
| WO | WO 2004/103430 A2 | 12/2004 |
| WO | WO 2004/105643 A1 | 12/2004 |
| WO | WO 2005/011463 A2 | 2/2005 |
| WO | WO 2005/011519 | 2/2005 |
| WO | WO 2005/011519 A2 | 2/2005 |
| WO | WO 2005/032422 | 4/2005 |
| WO | WO 2005/037152 A1 | 4/2005 |
| WO | WO 2005/060869 A1 | 7/2005 |
| WO | WO 2005/060882 A1 | 7/2005 |
| WO | WO 2006/161265 A1 | 4/2006 |

OTHER PUBLICATIONS

PCT International Search Report for PCT/US07/08882, mailed Dec. 26, 2007.
U.S. Appl. No. 11/431,040, filed May 2006, Kagan et al.
U.S. Appl. No. 11/548,605, filed Oct. 2006, Dann et al.
*Antireflux operations at flexible endoscopy using endoluminal stitching techniques: an experimental study*, Sritharan S. Kadirkamanathan et al., *Gastrointestinal Endoscopy*, vol. 44, No. 2, 1995 pp. 133-143.
*Progression rate of self-propelled feeding tubes in critically ill patients*, Mette M. Berger et al., *Intensive Care Med* Oct. 29, 2002, pp. 1768-1774.
*Iatrogenic Intussusception: a Complication of Long Intestinal Tubes*, Patricia Redmond, M.D., et al., *American Journal of Gastroenterology*, vol. 77, No. 1, 1982, pp. 39-42.
*Design and Testing of a New, Small Diameter, Single Stitch Endoscopic Sewing Machine*, C.P. Swain et al., *Abstracts Submitted to A/S/G/E/ 1990*, Vo. 36, No. 2, 1990, pp. 213,214.
*Synthetic Biodegradable Polymers as Medical Devices*, John C. Middleton et al., *Medical Plastics and Biomaterials Magazine MPS Article Index*, Mar. 1998.
*Experimental study on in situ tissue engineering of the stomach by an acellular collagen sponge scaffold graft*, Hori Y. Nakamura et al., Abstract, May 2001.
*Repair of Full-Thickness Defects in Alimentary Tract Wall with Patches of Expanded Polytetrafluoroethylene*, Daniel S. Oh, MD et al., Annals of Surgery 2002; 235:708-712.
*Stents in the small intestine*, Singh S, Gagneja HK, Abstract, Oct. 2002.
*Evaluation of porcine-derived small intestine submucosa as a biodegradable graft for gastrointestinal healing*, SG del la Fuente et al., Abstract, J. Gastrointest Surg Jan. 2003.
*Endoscopic suturing for gastroesophageal reflux disease: clinical outcome with the Bard Endocinch*, Richard I. Rothstein, MD et al., *Gastrointestinal Endoscopy Clinics of North America*, 13 (2003) pp. 89-101.
*Wilson-Cook sewing device: the device, technique, and preclinical studies*, Michael Rosen MD, et al., *Gastrointestinal Endoscopy Clinics of North America*, 13 (2003) pp. 103-108.
*Endoscopic full-thickness plication: the device, technique, pre-clinical and early clinical experience*, Ram Chuttani, MD, *Gastrointestinal Endoscopy Clinics of North America*, 13 (2003) pp. 109-116.
*Endoscopic Gastropexy and Crural Repair for Gastro-Esophageal Reflux: Transgastric Surgery Under Endoscopic Ultrasound Control II*, Anette Fritscher-Ravens et al. *Digestive Week* 2003 Abstract.
*Endoscopic suturing for treatment of GERD*, m. Brian Fennerty, MD, *Gastrointestinal Endoscopy*, vol. 57, No. 3, 2003 pp. 390-395.
*Effect of Duodenal-Jejunal Exclusion of a Non-obese Animal Model of Type 2 Diabetes*, Francesco Rubino, MD et al., *Annals of Surgery*, vol. 239, No. 1, Jan. 2004, pp.

*The LAP-BAND Solution*, BioEnterics Corporation, Brochurehttp://www.bioenterics.com/.
*Successful Uses in Approximation Ligation & Fixation using the Quik-Stitch, Endoscopic Suturing System*, Paré Surgical, Inc. Brochure 2001.
*Obesity Treatment*, Medical Innovation Developpement, Brochure.
*The Remote Controlled Sedish Band, The method of choice in modern treatment of morbid obesity*, Obtech Medical AG, Brochure.
*The Bard EndoCinch Procedure*, Introducing Endoscopic Technology for the Treatment of GERD.
*Microvasive Wallstent® Colonic and Duodenal Endoprosthesis*, Boston Scientific website, www.bostonscientific.com, Sep. 20, 2002.
*COOK® Wilson-Cook Medical GI Endoscopy*, Wilson Cook: Biliary/Pancreatic Stents, www.cookgroup.com, Sep. 20, 2002.
*ROSS.Com, Abbott Laboratories Online*, Product Handbook, T-Fastener Set.
*Bioabsorbable Polymers*, William B. Gleason, *University of Minnesota*, 1998.
*Cope Gastrointestinal Suture Anchor Set*, www.cookgroup.com, Cook Diagnostic and Interventional Products Advertisement 2000.
*LSI Solutions®*, SEW-RIGHT® SR 5, Advertisement received at ASBS Conference 2002.
PCT International Search Report, PCT/US2003/34822 mailed Feb. 4, 2004.
PCT International Search Report, PCT/US2004/44049 mailed May 30, 2007.
*Endoscopic suturing*, C. Paul Swain MD, *Balliere's Clinical Gastroenterology*, vol. 13, No. 1. pp. 97-108, 1999.
*Endoscopic Suturing of a Novel Gastroesophageal Antireflux Device (GARD) a Prelinary Report*, N. J. Godin et al., *Gastrointestinal Endoscopy*, vol. 43, No. 4, 1996.
*An endoscopic stapling device: the development of new flexible endoscopically controlled device for placing multiple transmural staples in gastrointestinal tissue*, C. Paul Swain, MD et al., *Gastrointestinal Endoscopy*, vol. 35, No. 4, 1989 pp. 338-339.
*An endoscopically deliverable tissue-transfixing device for securing biosensors in the gastrointestinal tract*, C. Paul Swain, MD et al. *Gastrointestinal Endoscopy*, 1994 vol. 40 No. 6 pp. 730-734.
*Development of a gastroplasty with variable diameter. Experimental study using artificial sphincters*, M. Merlini et al., 1992 Abstract.
*A through-the-scope device of suturing and tissue approximation under EUS control*, Annette Fritscher-Ravens, MD, et al., *Gastrointestinal Endoscopy*, vol. 56, No. 5, 2002, pp. 737-742.
*Bard EndoCinch: the device, the technique and pre-clinical studies*, Paul Swain, M.D. et al., *Gastrointestinal Endoscopy Clinics of North America*, 13, 2003 pp. 75-88.
*Microvasive gastric stapler: the device, technique, and preclinical results*, Tom R. De Meester MD, *Gastrointestinal Endoscopy Clinics of North America*, 13 (2003) pp. 117-133.
*Transgastric gastropexy and hiatal hernia repair for GERD under EUS control: a porcine model*, Annette Fritscher-Ravens, MD et al., *Gastrointestinal Endoscopy*, vol. 59, No. 1, 2004, pp. 89-95.
*T=Anchor Introducer Gun™ Details*, Moss™ Tubes Brochure.
SEW-RIGHT® SR 5™ & SR 10™, Ti-KNOT® TK 5™ Advertisement received at ASBS Conference 2002.
*Three-dimensional pressure image and muscular structure of the human lower esophageal sphincter*, Stein et al., *Surgery*, vol. 117, No. 6, Jun. 1995 pp. 692-698.
*Endoscopic vertical band gastroplasty with an endoscopic sewing machine*, Wan et al., *Gastrointestinal Endoscopy*, vol. 55, No. 2, 2002 pp. 254-256.
*A new method of enteroscopy—The double-balloon method*, Yamamoto et al., *Can J. Gastroenterol*, vol. 17, No. 4 Apr. 2003, pp. 273-274.
*Radiocontrolled Movement of a Robot Endoscope in the Human Gastrointestinal Tract*, paul swain et al., Abstract—*Gastrointestinal Endoscopy*, vol. 61, No. 5 DDW Abstract Issue: Apr. 2005.
*Techniques for Advancing Guide Wires and Devices in the Lumen of the Gastrointestinal Tract*, Long et al., *Gastrointestial Endoscopy*, vol. 57, No. 5 Apr. 2003 Abstract, 2003 ASGE Meeting, May 18-21, Orlando Florida.

* cited by examiner

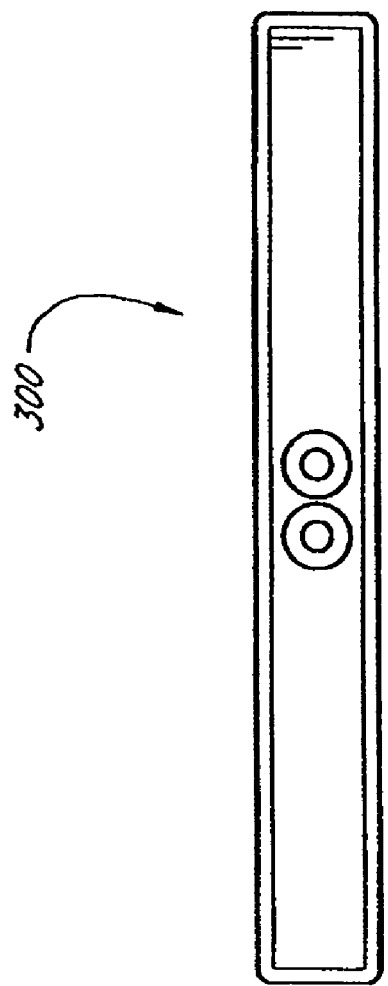
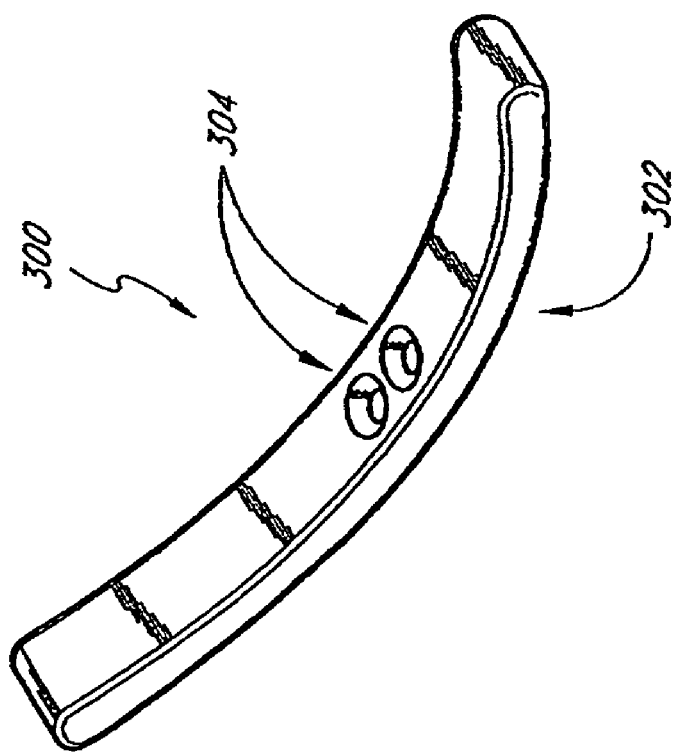
FIG. 7B
FIG. 7A

CUFF AND SLEEVE SYSTEM FOR GASTROINTESTINAL BYPASS

CROSS REFERENCE TO RELATED APPLICATIONS

This patent application is a continuation of Ser. No. 11/400,724 filed Apr. 7, 2006 which is a continuation-in-part of U.S. patent application Ser. No. 11/124,634 filed May 5, 2005 which claims the benefit of U.S. provisional patent application 60/569,442, filed on May 7, 2004, by Kagan et al. for Devices and Methods for Treating Morbid Obesity and U.S. provisional patent application 60/613,917, filed on Sep. 27, 2004, by Kagan et al. for Devices and Methods for Attachment of a Gastrointestinal Sleeve. This patent application is also a continuation-in-part of U.S. utility patent application Ser. No. 10/698,148, filed on Oct. 31, 2003 by Kagan et al. for Apparatus and Methods for Treatment of Morbid Obesity which claims priority to U.S. provisional patent applications 60/480,485, filed Jun. 21, 2003, 60/448,817, filed Feb. 21, 2003, 60/437,513, filed Dec. 30, 2002, 60/430,857, filed Dec. 3, 2002, 60/428,483, filed Nov. 22, 2002, and 60/422,987 filed Nov. 1, 2002. This patent application is also a continuation-in-part of U.S. utility patent application Ser. No. 10/998,424, filed on Nov. 29, 2004 by Kagan et al. for Apparatus and Methods for Treatment of Morbid Obesity and of U.S. utility patent application Ser. No. 11/025,364, filed on Dec. 29, 2004, by Kagan et al. for Devices and Methods for Treating Morbid Obesity. The devices and methods described herein can be combined with and/or used in conjunction with the apparatus and methods described in these prior applications. These and all patents and patent applications referred to herein are hereby expressly incorporated by reference in their entireties herein.

BACKGROUND OF THE INVENTION

1. Field of the Invention

The present invention relates to devices and methods for attachment of a device within a patient's digestive tract. In particular, the present invention relates to devices and methods for treatment of obesity and/or its comorbidities, such as diabetes.

2. Description of the Related Art

Bariatrics is the field of medicine encompassing the study of overweight, its causes, prevention and treatment. Bariatric surgery is a treatment for morbid obesity that involves alteration of a patient's digestive tract to encourage weight loss and to help maintain normal weight. Known bariatric surgery procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty. A more complete history of bariatric surgery can be found in U.S. Provisional Patent Application No. 60/422,987 Apparatus and Methods for Treatment of Morbid Obesity and also on the website of the American Society for Bariatric Surgery at http://www.asbs.org.

Medical sleeve devices for placement in a patient's stomach are described by Rockey in U.S. Pat. Nos. 4,501,264, 4,641,653 and 4,763,653. The medical sleeve described in these patents are said to reduce the surface area available for absorption in the stomach, however it is not configured to effectively reduce the volume of the stomach nor will the described isolate ingested food from stomach secretions. Other sleeve devices for placement in a patient's intestines are described in U.S. Pat. No. 4,134,405 (Smit), U.S. Pat. No. 4,315,509 (Smit), U.S. Pat. No. 5,306,300 (Berry), and U.S. Pat. No. 5,820,584 (Crabb). The sleeve devices described in these patents are said to be placed at the lower end of the stomach and therefore do not serve to isolate ingested food from the digestive secretions of the stomach.

In U.S. Patent Application US 2003/0040804, Stack et al. describe a satiation device to aid in weight loss by controlling feelings of hunger. The patent application describes an antral tube that expands into the antrum of the stomach to create a feeling of satiation. In U.S. Patent Application US 2003/0040808, Stack et al. describe a satiation device for inducing weight loss in a patient includes a tubular prosthesis positionable such that an opening at its proximal end receives masticated food from the esophagus, and such that the masticated food passes through the pouch and into the stomach via an opening in its distal end.

In U.S. Patent Application US 2003/0120265, Deem et al. describe various obesity treatment tools and methods for reducing the size of the stomach pouch to limit the caloric intake as well as to provide an earlier feeling of satiety. The smaller pouches may be made using individual anchoring devices, rotating probes, or volume reduction devices applied directly from the interior of the stomach. A pyloroplasty procedure to render the pyloric sphincter incompetent and a gastric bypass procedure using atraumatic magnetic anastomosis devices are also described.

In U.S. Patent Application US 2003/0144708, Starkebaum describes methods and systems for treating patients suffering from eating disorders and obesity using electrical stimulation directly or indirectly to the pylorus of a patient to substantially close the pylorus lumen to inhibit emptying of the stomach.

Not withstanding the foregoing, there remains a need for a perorally deployable device for the treatment of obesity and/or its comorbidities, as well as a way to attach the device and to position a bypass tube within the intestine.

SUMMARY OF THE INVENTION

There is provided in accordance with one aspect of the present invention, an attachment system for attaching a device to the mucosal side of a wall of the gastrointestinal tract. The wall comprises, among other tissue layers, a muscularis layer and a serosal layer. The system comprises a gastrointestinal attachment cuff having a tubular body, a proximal end and a distal end. At least one attachment structure (sometimes referred to as a tissue anchor) is provided for transmural attachment of the cuff to the mucosal side. The anchor comprises a connecting element (sometimes referred to as a tension element) for extending through the wall and at least one transverse retention surface for positioning in contact with the serosal tissue. The cuff may be a unitary annular component or assembly, or may comprise two or three or more components spaced circumferentially apart about a longitudinal axis.

The tension element may comprise a suture. The tension element comprises a proximal end for extending through the mucosal layer and a distal end for carrying the transverse retention surface. The transverse retention surface comprises a proximal surface of a serosal anchor: The serosal anchor may comprise a T-tag, a disk, or an inflatable structure. The serosal anchor is transformable between a first, reduced profile for distal transmural advancement through the wall, and a second, enlarged profile for resisting proximal retraction through the wall.

The tension element has a length between the cuff and the transverse retention surface, and the length is generally at least about 2 mm and often no more than about 20 mm. In some implementations of the invention, the length is within the range from about 2 mm to about 10 mm and, depending on the patient, potentially within the range from about 3 mm to about 6 mm. Preferably, the connecting element is at least as long as the uncompressed wall thickness of the tissue at the attachment point.

The attachment system may additionally comprise a first engagement surface carried by a first coupler on the attachment cuff for coupling to a second, complementary engagement surface carried by a second coupler on a gastric bypass tube. The first and second couplers may be configured for removable coupling or permanent coupling between the bypass tube and the cuff. The bypass tube may have a length of at least about 50 cm, at least about 75 cm and in certain embodiments at least about 100 cm. The length is generally at least long enough to place the distal end beyond the pylorus, and, preferably, beyond the ligament of Treitz. The system may comprise at least 6 tissue anchors, and, in some applications, at least 12 tissue anchors.

The cuff may be omitted and the proximal end of the bypass tube may be attached directly to the adjacent tissue. The use of a cuff may be preferred, however, if removal or replacement of the bypass tube is contemplated, or if it is desirable to separate the steps of tissue attachment and bypass tube placement.

There is provided in accordance with another aspect of the present invention, a method of attaching a device to the mucosal side of a wall of the gastrointestinal tract, the wall comprising a muscularis layer and a serosal layer. The method comprises the steps of providing a tension element, having a retention element thereon. The retention element is advanced through the wall from the mucosal side and the retention element is placed such that it is spaced apart from the muscularis by serosal tissue, and placed on the serosal surface. The device is directly or indirectly (e.g. through a grommet, with intervening connectors, etc) attached to the tension element, such that the device is positioned adjacent the mucosal surface. As used herein, mucosal surface is a term of directional orientation and refers to the tissue surface facing the interior of the body lumen such as the lower esophagus or stomach, which may be covered by a mucosal layer.

Changes may be caused to the serosal or other tissue following the attaching step. The changes may be caused to the tissue prior to the attaching step. The changes may be caused to the tissue as a biological response to tension on the tension element, biasing the retention element against the serosal surface. Alternatively, the changes may be caused to the serosal tissue in response to the application of an active agent. The active agent may comprise a growth factor, a sclerosing agent, or other agent or process for increasing the tissue density (e.g. initiating a fibrotic response) of the serosal tissue residing between the retention element and the muscularis.

In accordance with a further aspect of the present invention, there is provided a method of treating a patient. The method comprises the steps of providing a gastrointestinal attachment cuff having a tubular body, a proximal end and a distal end. The gastrointestinal cuff is positioned in the patient's digestive tract adjacent a mucosal surface in the vicinity of the gastroesophageal junction, the mucosal surface separated from a serosal surface by a wall thickness. The gastroesophageal cuff is secured adjacent the mucosal surface by advancing at least three tissue anchors through the mucosal surface, across the wall thickness and through the serosal surface to position a transverse retention surface of each tissue anchor in contact with the serosal surface. Preferably, the foregoing steps are accomplished endoscopically.

The securing step may comprise advancing at least 6 tissue anchors through the mucosal surface, and, in certain applications, at least 12 tissue anchors.

The tissue anchor comprises a tension element such as a suture for connecting the transverse retention surface to the cuff. The transverse retention surface may be a surface on a T-tag, a disk, or other retention structure. The length of the tension element may be at least about 75% of the wall thickness between the mucosal surface and the serosal surface. Preferably, the length of the tension element is at least about 95% of the wall thickness, and, optimally, the length of the tension element is at least about equal or greater than the wall thickness. In one embodiment the length of the tension element is at least about 120% of the wall thickness.

The method may additionally comprise the step of providing an elongate flexible gastric bypass tube having a proximal end and a distal end, and attaching the proximal end to the cuff. The proximal end of the bypass tube may be attached to the cuff endoscopically. The attaching the proximal end of the bypass tube to the cuff step may comprise removably attaching the proximal end of the bypass tube to the cuff. The distal end of the bypass tube may be positioned in the patient's jejunum, in the patient's ileum, or in the patient's duodenum.

The flexible gastric bypass tube may additionally be provided with an optional restrictive opening. The restrictive opening may be positioned anywhere along the length of the sleeve, preferably between the GEJ and the pylorus. The restrictive opening may be provided in any of a variety of ways, such as by including an additional annular component within the tubular sleeve, providing a restrictive band or component on the exterior of the tubular sleeve, or by molding or otherwise forming the restrictive opening as an integral part of the sleeve.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIGS. 7A-7B show two views of a T-tag embodiment of a tissue anchor.

DETAILED DESCRIPTION OF THE PREFERRED EMBODIMENT

The present invention provides devices and methods for attaching an implant within the gastrointestinal system. Although described primarily in the context of supporting an endolumenal bypass sleeve, the attachment technology of the present invention can be utilized to support any of a variety of devices which may be desirably positioned within the stomach or elsewhere in the gastrointestinal system. For example, the attachment cuff and/or serosal anchors disclosed herein may be utilized to support any of a variety of valves or constricted openings designed to treat gastroesophageal reflux disease (GERD), by augmenting natural function of the lower esophageal sphincter or replacing that function. Any of a variety of obesity devices may also be attached to the attachment cuff and/or using the serosal anchors disclosed herein, such as electrical stimulation and/or pacing devices, or volume occupying devices which hang from or are otherwise attached to the vicinity of the lower esophageal sphincter into the stomach. Any of a variety of drug delivery reservoirs may also be stabilized within the gastrointestinal system using the cuff and/or anchoring systems disclosed herein. Diagnostic devices, such as pH detectors, analyte detectors, pressure sensors may also be temporarily or permanently secured within the gastrointestinal system using the technologies disclosed herein. The attachment cuff and/or associated serosal anchors may further be utilized to accomplish endolumenal anastomosis, or to span a defect or disease condition, such as an ulceration or other gastrointestinal anomaly.

Not withstanding the foregoing, the present invention will be described primarily in the context of gastrointestinal sleeve devices that can mimic a Roux-en-Y gastric bypass by effectively reducing stomach volume, bypassing a portion of the stomach and/or small intestines, reducing nutrient absorption in the stomach and/or small intestines and depositing minimally or undigested food farther than normal into the intestines, thereby stimulating intestinal responses.

Figure 1:
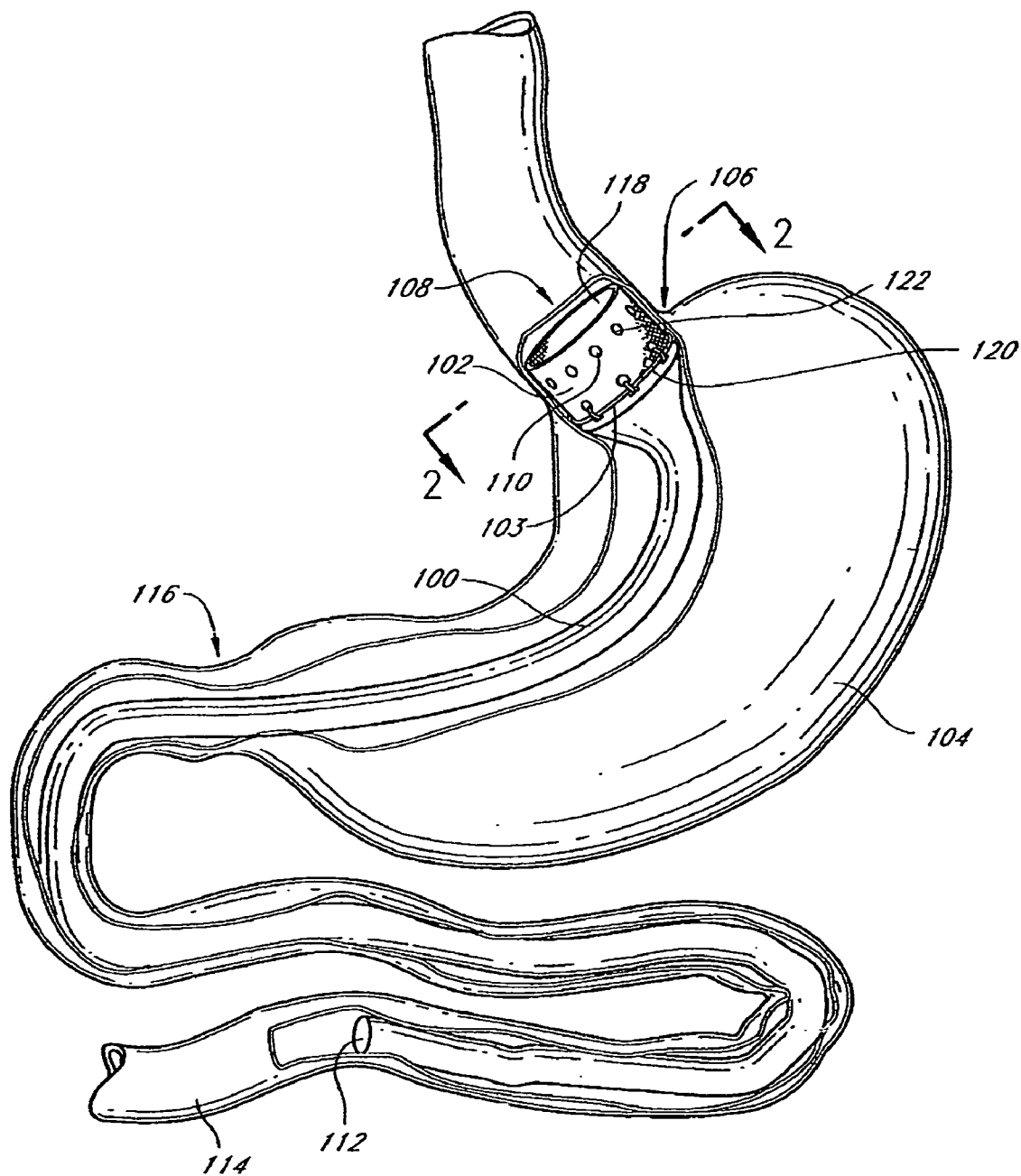
FIG. 1 shows a gastrointestinal sleeve device attached to a cuff positioned in the vicinity of the gastroesophageal junction.

FIG. 1 shows a gastrointestinal sleeve device 100 attached to an artificial attachment cuff or stoma device 102 implanted within a patient's stomach 104. The attachment cuff 102 can be implanted in the vicinity of the gastroesophageal junction 106, or at the outlet of a surgically created gastric pouch (not illustrated). The attachment cuff 102 preferably does not restrict the flow of food, although it may be provided with a restrictive opening if desired. The cuff 102 can have a fixed diameter opening 108 equal to, larger or smaller than the fully open diameter at the native GEJ. Alternatively, the cuff 102 can have an adjustable stoma opening or it can be a "smart" stoma that adjusts the size of the stoma opening in response to various conditions.

The attachment cuff 102 is preferably configured for per-oral delivery and attachment using endoscopic techniques. Alternatively, the cuff 102 can be implanted using laparoscopic or open surgical techniques. Additional details of the cuff, stoma and attachment are found below, and in the related applications previously incorporated by reference herein.

The gastrointestinal sleeve device 100 is an elongated flexible tubular structure that is permanently or removably attached to the attachment cuff 102 such that food and liquids pass through the cuff 102 and enter the internal lumen of the sleeve device 100. The attachment cuff 102 and the gastrointestinal sleeve device 100 can be implanted simultaneously, or the attachment cuff 102 can be implanted by itself and then the gastrointestinal sleeve device 100 can be attached to the attachment cuff 102 in the same or a subsequent procedure. Optionally, a line of staples or other fasteners may be used with any of the devices disclosed herein to create a gastroplasty to reduce the volume of the stomach.

In conjunction with the cuff and/or gastric sleeve, the volume of the stomach can be reduced by suturing, stapling, adhesives or other technique using open, transesophageal or laparoscopic techniques. Alternatively or in addition, a gastric balloon or other volume displacement device may be used in conjunction with the gastric sleeve to provide a feeling of satiety. These adjunctive techniques may have the effect of further reducing nutrient intake (in the case of a stomach reduction and pouch formation upstream of a stoma) and enhancing the effect of peristaltic motions of the stomach for moving food through the gastric sleeve intake (in the case of a stomach reduction downstream of a stoma where there is a gastric sleeve).

Returning to FIG. 1, a gastrointestinal sleeve device 100 is attached at the GEJ with an attachment cuff 102. Tissue anchors, described below, have been omitted from FIG. 1 for simplicity. The cuff 102 may include a plurality of preformed attachment structures 110 for attachment of tissue anchors as is discussed below.

The implantable cuff and/or attachment system is preferably configured to avoid causing excessive force or pressure within the tissue by having compliance that is compatible with the gastrointestinal tissues where it is attached. Device compliance can also be important for providing a leak free seal between an implanted device and the tissue at the attachment point. Compliance can be provided in the radial or circumferential direction and/or in the vertical, axial or longitudinal direction. The device may have different compliance in different regions to be compatible with the tissue at the attachment point and at other portions of the gastrointestinal tract through which it runs. The device may have different compliance in different directions to be compatible with the tissue at the attachment point while simultaneously achieving other goals of the device. Compliance can be provided in a number of different ways. One way is by elastic or plastic deformation of the device and/or the attachment means. Another way is by a mechanical decoupling that allows relative movement between the device and the attachment points, and/or between the attachment points themselves, without transmitting excessive force or pressure to the tissue.

In some clinical situations, it will be desirable to match compliance between the device and the tissue to which it is attached. In other situations, based upon the clinical situations, it may be desirable to provide a device with higher or lower compliance than the adjacent tissue to achieve certain objectives.

Preferably, the attachment cuff 102 is highly flexible or compliant in the radial direction so that expansion and contraction of the stomach and esophagus due to contents and/or muscular action will not place additional, or actually reduce, stress on the attachment points. An elastomeric material, such as silicone or polyurethane that provides approximately 150% or more stretch in the radial direction may be used. At the same time, an attachment ring or other structure for attaching the sleeve, where utilized, may have enough lateral rigidity to act as a mounting platform for the gastrointestinal sleeve device and to resist downward movement due to the weight of the gastrointestinal sleeve device and its contents and peristaltic traction on the sleeve. The lateral rigidity of any sleeve attachment structure can be enhanced with radially oriented bending reinforcements, such as ribs or embedded reinforcement members. Alternatively, the attachment cuff can be flexible and compliant and other means such as hooks, sutures staples, etc., can be used for sleeve attachment.

Referring to FIG. 1, the attachment cuff 102 comprises a highly flexible tubular wall extending between a proximal (superior) end 118 and a distal (interior) end 120. The wall may be permeable or substantially impermeable to body fluids, and may comprise any of a variety of weave densities and/or aperture patterns either to effect flexibility, fluid transport, or to accommodate attachment as is discussed further below.

The axial length of the cuff 102 between the proximal end 118 and distal end 120 can be varied considerably, depending upon the desired attachment configuration. In general, axial lengths within the range of from about 0.25 inches to about 6 inches will be used. Axial lengths within the range of from about 0.5 inches to about 2.0 inches may be sufficient to support a detachable endolumenal bypass sleeve as contemplated herein. In general, the axial length of the attachment cuff 102 may be influenced by the desired location of the seam 103 between the attachment cuff 102 and the sleeve 100, or other device which is to be attached to the cuff 102.

The attachment cuff 102 may be constructed from any of a variety of materials which are sufficiently flexible and stable in the environment of the stomach. Suitable materials may include woven or nonwoven fibers, fabrics or extrusions using materials such as polyester velour (Dacron), polyurethane, polyamide, ePTFE, various densities of polyethylene, polyethylene terephthalate, silicone, or other materials which in the form presented exhibit sufficient compliance, stretch, strength, and stability in the gastric environment.

The inside diameter of the cuff 102 can also be varied, depending upon the desired clinical performance. For example, the cuff may be provided with a stoma or inside diameter which is less than the inside diameter of the adjacent esophagus. Alternatively, the inside diameter of the cuff 102 may be approximately equal to or even greater than the native esophagus. In general, inside diameters within the range of from about 15 mm to about 40 mm are contemplated, and often within the range of from about 20 mm to about 35 mm for use in human adults.

In the illustrated embodiment, the cuff 102 is provided with a plurality of attachment structures 110 in the form of apertures 122. These apertures 122 are provided to facilitate anchoring of the cuff 102 to the adjacent tissue. In either an endoscopic or surgical implantation, a plurality of tissue anchors will be pre-attached to, or advanced through the wall of the cuff 102 and transmurally through the adjacent tissue as is discussed elsewhere herein. Provision of a plurality of anchoring points such as apertures or other structures which facilitate positioning and/or attachment of tissue anchors may desirably help with anchor location as well as reduce the amount of force necessary to advance t-tags or other anchoring structures through the wall of the cuff 102.

In an embodiment which utilizes apertures 122 to facilitate tissue anchoring, the number of apertures 122 may correspond to or be greater than the total anticipated number of tissue anchors. In general, at least about four apertures 122 and as many as eighteen or twenty are presently contemplated, with from about eight apertures to about sixteen apertures presently preferred. In one embodiment, twelve tissue anchors are used.

Preferably, the apertures 122 in an embodiment of the cuff 102 made from a thin walled woven or non-woven material will be provided with a reinforcement ring (one reinforcing ring per aperture, or one reinforcing ring for the implant, superior to the apertures 122) to prevent pull-out of the associated anchoring structures, as will be appreciated by those of skill in the art in view of the disclosure herein. The reinforcement ring, where used, may be a separate component such as a grommet attached at each aperture to the cuff 102 such as by thermal bonding, adhesives, mechanical interference or other technique. Alternatively, particularly in the case of a fabric cuff 102, the reinforcement may be provided by stitching around the perimeter of the aperture 122 in the manner of a buttonhole as is understood in the art.

In the illustrated embodiment, each of the plurality of apertures 122 resides in a common transverse plane, positioned in the patient at or slightly above the gastroesophageal junction. Alternatively, the apertures 122 may be provided in two or three or more transverse planes, such as to permit attachment points in a zig-zag orientation around the circumference of the attachment cuff 102. For example, a first set of apertures 122 (such as every other aperture) may be axially displaced from a second set of apertures 122 by a distance within the range of from about 1 mm to about 10 mm, to provide a first and a second transverse attachment plane. Axially staggering the location of the attachment apertures 122 may be desirable depending upon the number and configuration of tissue anchors and tissue anchor reinforcement structures as may be apparent to those of skill in the art in view of the disclosure herein.

Figure 3:
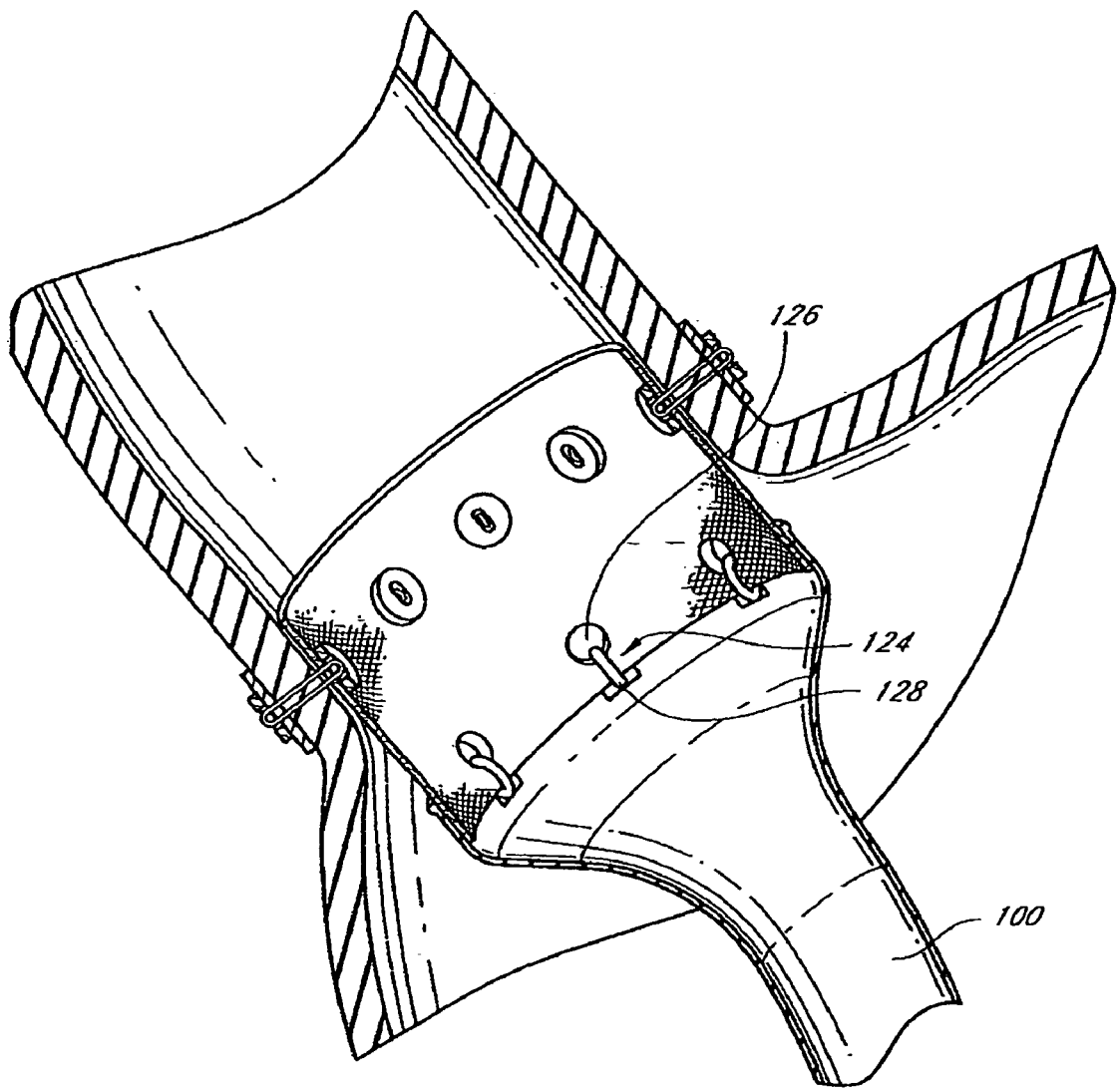
FIG. 3 is an enlarged cross sectional view of the cuff of FIG. 1.

Referring to FIG. 3, a plurality of attachment points 124 may also be provided on the cuff 102, for permanently or removably attaching the bypass sleeve 100. In the illustrated embodiment, the attachment points 124 each comprise an aperture 126 for receiving a suture hook, clip or other interference coupling, magnet assisted coupling or other link 128 to couple the bypass sleeve 100 to the cuff 102. The bypass sleeve 100 may be attached to the cuff 102 in any of a variety of ways, such as is discussed elsewhere herein. In general, the present inventors contemplate a releasable attachment between the sleeve 100 and cuff 102, to permit removal and/or exchange of the sleeve 100 as has been discussed elsewhere herein.

Figure 2:
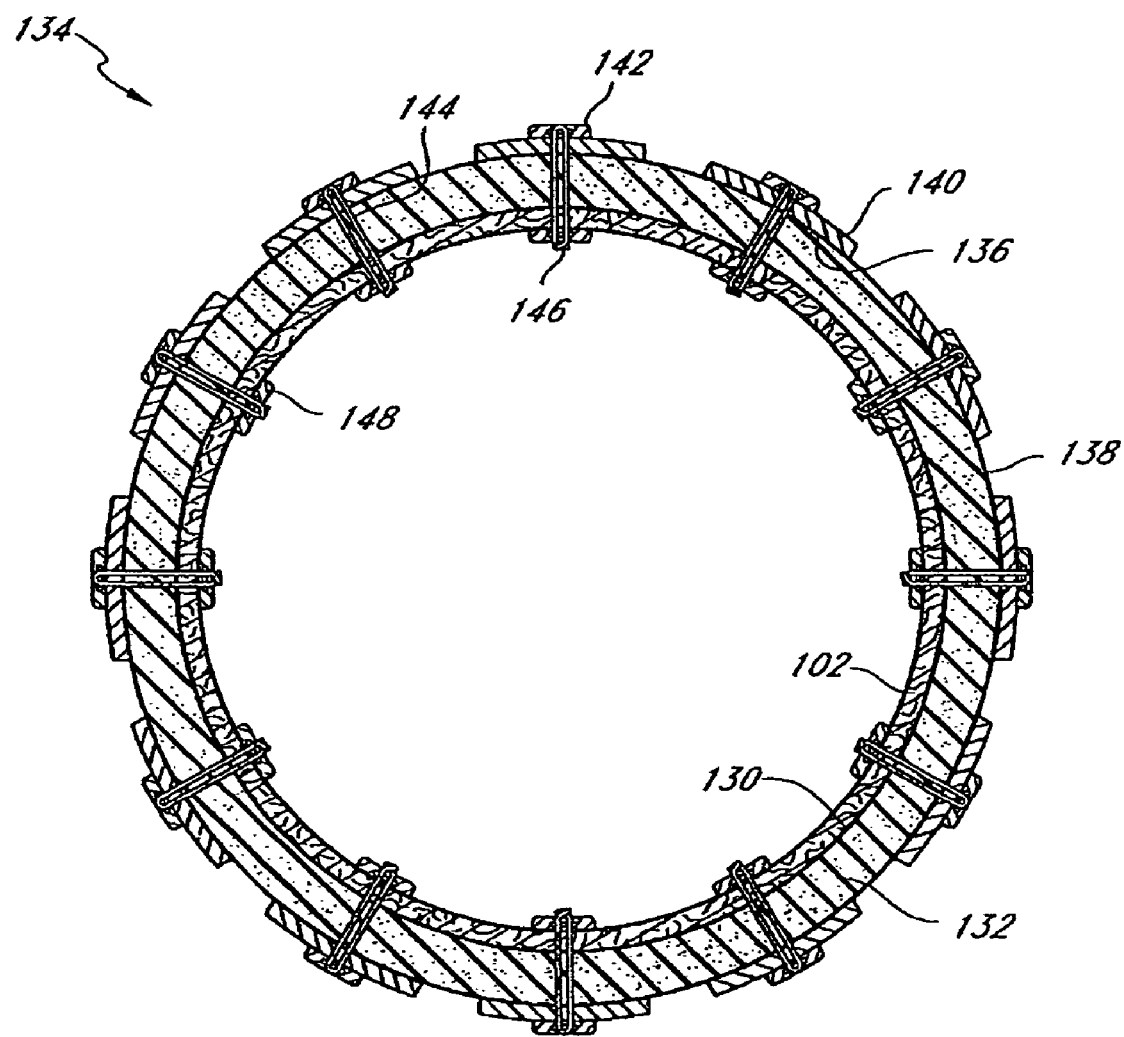
FIG. 2 is a cross sectional view taken along the line 2-2 in FIG. 1.

Referring to FIG. 2, there is illustrated a cross sectional view transverse to the longitudinal axis of the esophagus through the tissue attachment plane. Although the cuff 102 and tissue anchors appear rigidly geometric in the illustration, it is to be appreciated that the configuration will be subject to constant motion and random configuration, as the wall of the esophagus and stomach collapse and expand, with as little resistance as possible from the cuff 102 and associated attachment structures.

In FIG. 2, the cuff 102 is illustrated as snugly fitted against the mucosal surface 130 of the esophageal or stomach wall 132. A plurality of anchor assemblies 134 are shown for illustration purposes. The particular anchor assemblies 134 illustrated in FIGS. 2 and 3 may be best suited for surgical implantation, while some of the t-tag embodiments disclosed elsewhere herein may be more readily adapted for endoscopic implantation. The anchor assemblies 134 are therefore provided for illustration purposes, but should be understood as only a single example of the broader transmural, serosal surface anchoring of the present invention.

Referring to FIG. 2, the anchor assembly 134 comprises a transverse retention surface 136 for positioning against the serosal surface 138 of the esophagus or stomach wall (illustrated as a single, homogenous layer for simplicity). The transverse retention surface 136 may be a surface on a t-tag, disc, or other structure. In the illustrated embodiment, the surface 136 is carried by a small circular or oval button 140, although T-tags and other structures disclosed herein may be used, all of which are adapted to distribute force over a predetermined surface area. The button 140 may comprise any of a variety of materials, and, in one embodiment, comprises a silicone disc.

Due to the physical characteristics of silicone, a reinforcement element 142 in the form of a smaller disc or transverse structure may be embedded within, or provided on the radially outwardly facing surface of the disc 140. This reinforcement element 142 allows distribution of force from the tension element 144 across a greater surface area on the disc 140, to avoid "cheese cutter" effects or other pull through under tension exerted on the tension element 144. The desirability of including a separate reinforcing element 142 will go down, as the durometer or other rigidity characteristic of the disc 140 increases. Element 142 may comprise any of a variety of materials which will be biocompatible and generally stiffer than the disc 140, such as any of a variety of polyethylenes, PEEK, PEBAX or other materials well known in the art.

In the illustrated embodiment, the tension element 144 comprises a suture which extends from the inside of the esophagus transmurally to the reinforcing element 142 and loops back through the wall of the esophagus where it is clipped, tied, locked or otherwise secured at a connection point 146. The tension element may comprise either a single filament, or two or more filaments as illustrated, depending upon the desired installation technique and physical properties of the final construct.

A second reinforcing element 148 may also be provided, to serve the analogous function as the first reinforcing element 142, and resist pull through of the tension element 144 under the influence exerted on the implant by peristalsis and other gastrointestinal movement. The second reinforcing element 148 may be in the form of a disc, T-tag or other structure having a force distributing surface thereon. Alternatively, reinforcing element 148 may be a thickened, treated or reinforced zone on or within the wall of the sleeve. Additional details of t-tag attachment and related structures will be provided below.

Figure 4:
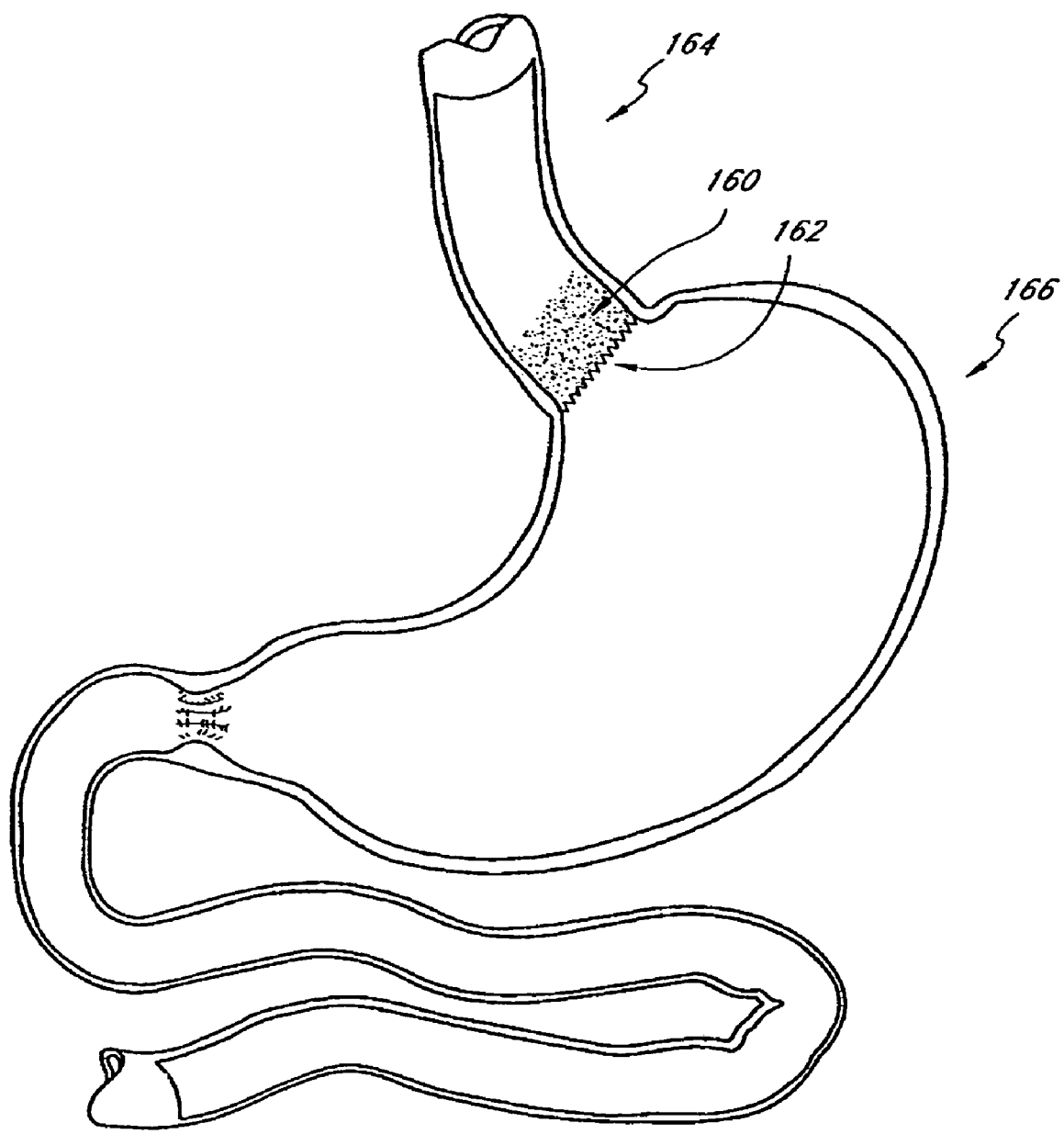
FIG. 4 shows a schematic illustration of the GEJ and the SCJ or Z-line and the target zone identified by the present inventors.

The present inventors believe that some areas of the esophageal or gastric wall exhibit physical properties more conducive to retaining attachment structures than other areas. For example, an attachment zone 160, shown in FIG. 4, directly above the squamocolumnar junction (SCJ) 162, also known as the Z-line, ora serrata, and mucosal GEJ, may be such an area. The SCJ marks the junction of the squamous mucosa of the esophagus and the columnar or glandular mucosa of the stomach. The SCJ may be located at or below the lower esophageal sphincter (LES).

The device may, in one preferred embodiment, be attached in an attachment zone 160 no more than about 2 cm and preferably no more than about 1 cm above the SCJ 162 and below the esophagus 164 where the squamous mucosa is thicker than the squamous mucosa of the esophagus 164 and where there exists a serosal outer surface not exhibited at the esophagus 164. The thicker layer of squamous mucosa in the attachment zone 160 terminates distally at the endoscopically visible transition to the glandular mucosa of the stomach 166 which occurs at the SCJ 162. The device is also preferably attached at a location in the attachment zone 160 so as to minimize the risk of reflux. The SCJ 162 can be located relative to other anatomical regions. It normally may be found at the gastroesophageal junction (GEJ). The GEJ is the region at which the tubular esophagus joins the saccular stomach. The GEJ can be considered the first part of the stomach 166 or the cardia and is located at the proximal margin of the longitudinal gastric mucosal folds or in the distal 2 cm of the esophagus 164 and proximal stomach 166. Endoscopically, the location of the GEJ can be approximated by identifying the proximal margin of the gastric folds.

Thus, a first aspect to the location of attachment of the devices disclosed herein relates to the position of the attachment structures along the axis of the hollow lumen or organ. As described above, the attachment location in the axial direction is preferably in the vicinity of the gastroesophageal junction, and particularly just above the SCJ. This attachment site can be located endoscopically by observing the color change which occurs at the SCJ, and retracting or positioning the attachment structures of the endoscope slightly above that line.

A second aspect to the location of the attachment structure relates to the depth within the adjacent tissue wall (i.e., in a transverse direction to the longitudinal axis of the esophagus described above) within which the various anchors or retention structures disclosed herein reside. Applicants believe that the location in the transverse direction is subject to migration or other change post-implantation, as described in connection with FIGS. 5A through 5C.

Figure 5A:
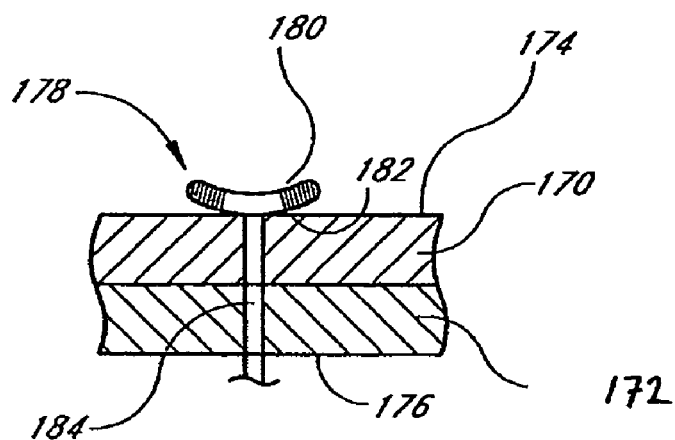
FIG. 5A shows a schematic illustration of a tissue anchor placed adjacent the serosa at the time of implantation.

Referring to FIG. 5A, there is disclosed a highly simplified schematic cross sectional view of a tissue wall such as the wall of a hollow organ or lumen in the body, including the wall at the vicinity of the gastroesophageal junction. The tissue wall comprises a serosa 170 and a muscularis 172. Additional tissue layers have been omitted for simplicity. In general, as is appreciated by those of skill in the art, the serosa 170 is on the outside of or faces away from the stomach, and the muscularis is on the inside, or faces towards the interior of the stomach. The serosa 170 thus includes a serosal surface 174 which faces away from the interior of the stomach, and the muscularis 12 includes a muscularis surface 176 which faces towards the interior of the stomach.

Figure 5B:
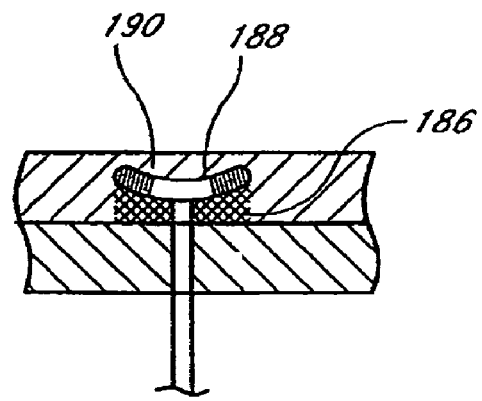
FIG. 5B shows a schematic illustration as in FIG. 5A, at a post implantation stage when the anchor has relocated into the serosa, and a layer of increased tissue density has formed on a proximal side of the tissue anchor.
Figure 5C:
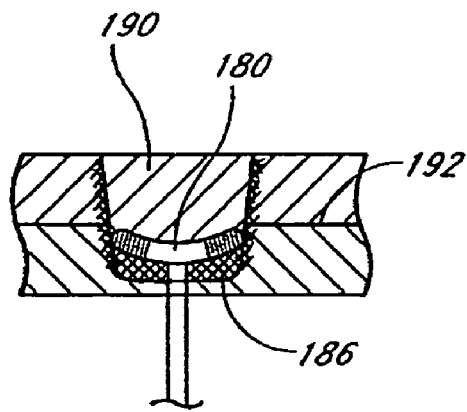
FIG. 5C is a schematic illustration as in FIG. 5B, with the anchor relocated proximally into the plane of the muscularis.

An attachment device or anchor 178 is illustrated in part in FIGS. 5A through 5C. The attachment device 178 can take any of a variety of forms, described elsewhere herein. In general, the attachment device 178 includes a retention element 180 having at least one retention surface 182 thereon. The retention element 180 may be integrally formed with or attached to a tension element 184, which extends through the tissue wall and is secured to the device implanted within the gastrointestinal tract. Although the attachment mechanisms disclosed herein will be defined primarily in the context of an obesity device, which is attached in the vicinity of the GEJ, those of skill in the art will appreciate that the attachment system disclosed herein may be utilized in any of a wide variety of other anatomical locations, such as in the bronchial tubes, urethra, ureters, fallopian tubes, throughout the GI tract, and others which share a serosa or serosa like layer, such as in the kidney, bladder, and other organs, as would be recognized by those skilled in the art.

Referring to FIG. 5A, the retention element 180 is illustrated with the retention surface 182 residing against the serosal surface 174. Retention surface 182 may comprise any of a variety of forms, such as a proximal surface on a T-tag, proximal surface on a washer or disc, or any other surface which extends in a generally lateral direction with respect to a longitudinal axis of the tension element 184. The transverse retention surface 182 may be radially enlargeable or expandable from a first, reduced cross-sectional configuration to provide a low crossing profile such as for deployment through a deployment cannula, and a second, radially expanded or enlarged cross-sectional profile as illustrated in FIG. 5A, to provide a retention surface 182 which will engage or interfere with tissue of the serosa 170 or muscularis 172 to resist proximal retraction of the attachment device 178 through the tissue. Transformation between the first configuration and second configuration can be accomplished in any of a variety of ways as is discussed further herein, such as by pivoting the retention element 180 about the attachment point to tension element 184, by radial expansion, by inflation, or other technique.

Tension element 184 may comprise any of a variety of connectors or elements adapted to extend through the tissue wall, such as a suture, or other single stand or multi-strand filament or material. In some embodiments the tension element 184 is formed of a polymer such as PEEK or silicone. The tension element 184 may also, in some embodiments, have elastic properties. In other embodiments the tension element 184 does not have elastic properties. By use of the term tension element, no specific mechanism is suggested, and the element is not required to be under mechanical tension.

The attachment device, otherwise sometimes referred to herein as a tissue anchor, T-tag or other label, it is illustrated in FIG. 5A in a schematic fashion as it may appear at the time of implantation. Since in certain implementations of the invention the length of the tension element 184 will exceed the uncompressed thickness of the adjacent tissue wall, the retention surface 182 may even be spaced slightly apart from the serosal surface 174 depending upon the transient motion or configuration of the stomach at any given time.

Without being limited to any particular structure or mechanism, Applicants believe that the presence of the attachment device may cause or accelerate the formation of a layer 186 of serosal tissue having increased tissue density relative to unaffected or normal serosal tissue. The layer of increased density 186 may result from a process in which the transverse retention surface 182 places pressure against the serosa 170, causing a localized necrosis due to the restriction of capillary blood flow. The necrosed tissue thereafter fibroses, as a part of a normal healing response. The layer of increased density 186 or fibrosis may also result from a foreign body reaction triggered by the presence of the transverse retention surface 182. Applicants have observed a greater degree of fibrosis or denser tissue on the side of the T-tag facing the lumen of the stomach, for example on the retention surface 182.

In certain animal trials conducted by Applicants in which the animals were sacrificed five weeks following implantation of the attachment device 178, successful anchors appeared similar to the simplified schematic illustration of FIG. 5C. In this illustration, the location of the retention element 180 has changed relative to the serosa 170 and muscularis 172, and the distal surface 188 of the retention element 180 has been covered with an overgrowth of serosal tissue 190. A fibrotic layer 186 is positioned in between the retention surface 182 and the muscularis 172. Although illustrated only on the proximal side of the retention element 180 where the greatest degree of fibrosis has been found to occur, the fibrotic response appears to some extent to surround and wall off the entire retention element 180.

It appears to the present inventors that formation of a sufficient fibrotic response on the proximal side of the retention surface 182 decreases the likelihood that the attachment device 178 will relocate to the inside of the stomach under normal agitation of the stomach, changes in the thickness of the stomach wall, and other conditions normally occurring in the stomach. A similar response is schematically illustrated in FIG. 5C, in which the layer 186 of high density serosal tissue remains on the proximal side of the retention element 180, however one or both of the layer 186 and retention element 180 have relocated to below the normal plane 192 separating the serosa 170 from the muscularis 172 and will remain there.

It appears to the present inventors that if the device design and/or retention element 180 design are such that in normal use the retention element 180 relocates to a position in the muscularis 172 and past the serosa 170 before a sufficient fibrotic response, the retention element 180 may relatively easily pass through the muscularis 172 and failure will result. Thus, it may be desirable in certain implementations of the invention to facilitate or accelerate the formation of the fibrotic layer 186. This may be accomplished in any of a variety of ways which will be appreciated by those of skill in the art in view of the present disclosure, such as by the introduction of an active agent which will trigger a fibrotic response. Suitable active agents may include any of a variety of growth factors, and/or chemical sclerosing agents which are well known for other medical applications. The surfaces of the retention element and tension element may also be provided with an anti-bacterial characteristic, such as by eluting an antibiotic agent, or having a bacteriostatic or bacteria inhibiting coating. Drug eluting coatings are well understood in the coronary stenting arts, and can be adapted for use in the present context by those of skill in the art.

Active agents may be applied as a coating to the retention surface 182 or retention element 180, or may be impregnated into the material of retention element 180 and/or tension element 184, such as to permit a timed release into adjacent tissue. Incorporation may be accomplished by loading the active agent into tortuous pathways or pores exposed to the surface of the retention element 180, or by inclusion in a bioabsorbable or bioerodable carrier attached to or positioned in the vicinity of the retention surface 182. Energy sources may also be utilized, such as to generate heat or otherwise stimulate formation of a fibrotic response, as is discussed further below. Formation of the fibrotic layer 186 may also be facilitated by mechanical means, for example, in one embodiment, by roughening the retention surface 182 with the addition of fibrotic layer enhancement structures such as a plurality of bumps or etched lines.

Figure 6B:
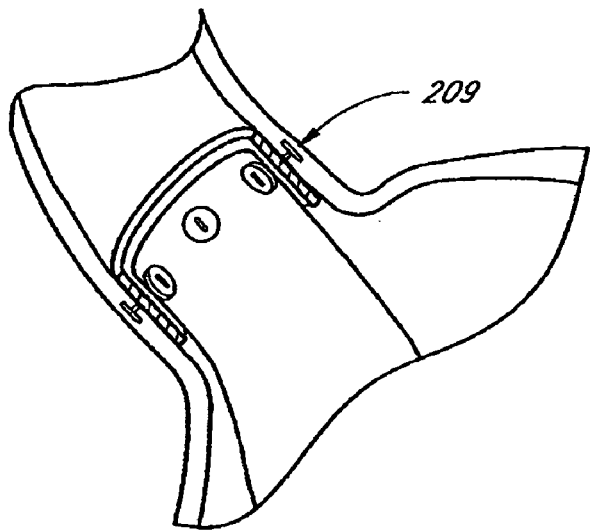
FIGS. 6A-6B show an attachment cuff attaching a gastrointestinal sleeve device using T-tags secured with a button.
Figure 6A:
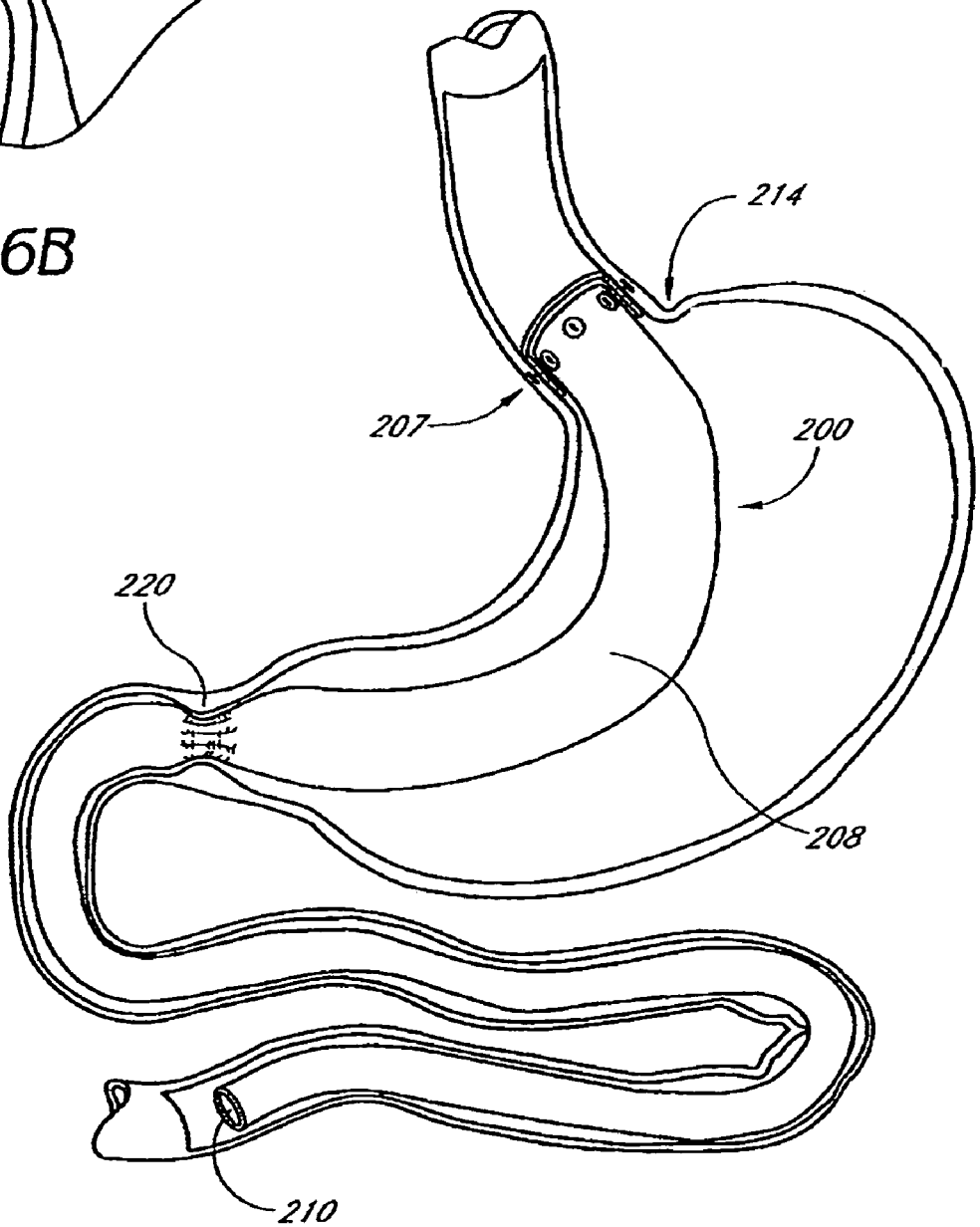

FIG. 6A shows an implanted gastrointestinal sleeve device 200 attached by an attachment cuff 214 with the use of T-tags 207. FIG. 6B is an enlarged view of the attachment cuff 214 attached with T-tags 207 showing the transverse retention elements 209 of the T-tags 207 embedded in the stomach wall, as may be observed several weeks post implantation.

T-tag type fasteners can be used endoscopically to attach many of the structures described herein. A T-tag is basically a retention element 180 in the form of a cross member or "T" that is attached to a tension element 184 in the form of an elongated member or tail at or near the mid-point of the T. A "stem" may be a structure at the joining point of the T and tail. From the perspective of a peroral attachment technique, in which the attachment devices are preferably advanced through muscularis 172 in the direction of the serosa 170, the stem or tension element will be referred to herein as relatively proximal to the cross member on the T-tag. The T-tag is a member of a more general family of tissue anchors, in which a proximally facing surface 182 (such as the proximal surface of the cross member) is adapted to be bent, folded, or otherwise reduced in crossing profile to a first configuration in which it can be advanced distally through a relatively small tissue opening, to a second configuration in which it presents a proximal serosal surface contacting area for resisting proximal retraction through the access pathway. Thus, although described primarily in the context of a T-tag and variations thereof, the present invention relates more broadly to tissue anchors of the type for presenting a retention surface which may have any of a wide variety of configurations. Some are described in additional detail below. The stem may also be referred to herein as a tension member, and may comprise a suture, or other single strand or multi-strand element for drawing the tissue anchor against the serosal tissue and/or connecting the tissue anchor to the implantable cuff or other endolumenal implant.

T-tag fasteners are generally configured to flex or pivot at the juncture of the T and tail to allow delivery along the axis of the T through a minimal puncture diameter. T-tag fasteners can be configured with an extended tail that may extend out the mouth and optionally be used to parachute devices for attachment into position in vivo. Other T-tag configurations can include, crimp, snap, screw or other means of securing the T-tag tail when appropriate. One embodiment of a T-tag fastener could include a dual tail. Such a dual tail could be combined with extended tails that could then be tied outside the body with the ensuing knots then tightened within the body. Such a dual tail could be constructed of one of a number of non-biodegradable suture materials known in the art including polypropylene, nylon, braided Dacron or silk. In some clinical situations biodegradable tails could be indicated and could be constructed using materials described herein. In a preferred embodiment the tails could be constructed of a monofilament material.

In certain implementations of the present invention, it may be desirable to increase the effective surface area of the retention surface 182. This may be accomplished using any of a variety of disc or button shaped attachment devices 178 disclosed herein, or by introducing a buttressing component or element in the nature of a washer or other structure for enlarging the effective surface area. This buttressing structure may sometimes be referred to herein as a pledget. The buttressing material is generally configured perpendicular to the axis of the tension element 184 (e.g. suture, rivet or staple) and therefore best distributes forces along the axis of the attachment means.

T-tags or other serosal anchors can be delivered through a hollow needle type delivery system (e.g. T-ANCHOR INTRODUCER GUN (Moss, Moss Tubes)) that has been redesigned/modified so it can be passed through the working channel of an endoscope. A T-tag can be provided with an elongated tail that can extent out through the mouth and be used to parachute structures into place in-vivo.

In one embodiment the T-tags are placed such that the sutures of the T-tags could be knotted outside of the body and the knots could be pushed down the working channel or outside of the working channel of the scope until positioned to retain the cuff. The suture tails could subsequently be removed. To facilitate management of all the suture tails, two T-tags could first be placed to secure the cuff followed by placement of the rest of the T-tags. In a preferred embodiment the T-tag tension elements, such as tails, sutures, or other structures as described herein, would terminate in the stomach, such as by tied knots, sliding buttons, or preexisting terminated ends, such that they would not need to be brought outside of the body.

As an alternative to tying sutures outside of the body, any of a variety of suture locks may be utilized to secure the suture with respect to the cuff. In general, a suture lock is provided with a central aperture for moveably receiving the suture therethrough. The lock may be configured for one way advance along the suture, having a spring biased engaging element for resisting movement of the lock in the opposite direction. Alternatively, a central plug may be advanced into the central lumen, to compress the suture within the suture lock and retain the suture lock at a selected position. Any of a variety of clips may also be axially or radially moved into position, to engage the lock with the suture. The suture lock may be advanced down the suture and positioned with the desired tension against the interior surface of the cuff, and activated as necessary to lock the suture lock in place. The remaining suture tail may be severed, using conventional endoscopic techniques.

Alternatively, the suture lock may be secured to the cuff 102 such as at each aperture 122, prior to implantation of the cuff 102 in the patient.

Many of the serosal anchors described herein can be formed using a single piece of Polypropylene, Nylon, PEEK, silicone, or other polymeric material well known in the art for use in construction sutures, which forms the "T" and tail as a single unit. Alternately two different materials can be combined, for example by insert molding, to achieve different properties of the "T" and tail. In another embodiment this could be combined with a "T" portion that is coated with a material selected for specific clinical properties such as encouraging or discouraging either in-growth or adhesion. The "T" portion may also be surrounded by another material such as ePTFE or Dacron graft material. "T" diameter or serosal surface contacting width can vary for example ranging from 0.5 mm to 3.0 mm in diameter for nylon or polypropylene with the typical "T" having a diameter of 1-2 mm. A tail could be the dimension of a standard suture and could generally vary from 5-0 to 0 (USP standard classification) though smaller or larger sizes may be appropriate in certain clinical situations.

FIGS. 7A & 7B illustrate a curved T-member 300 for a T-tag fastener. The convex curved tissue-contacting surface 302 of the curved T-member 300 serves to distribute the attachment force for an implanted device smoothly across the tissue to minimize any stress concentrations or higher pressure spots that could cause tissue necrosis and/or erosion. The T member 300 has a double eyelet 304 for attachment of a suture or other filament. The T-member is preferably molded of a fairly rigid, high strength biocompatible polymer such as PEEK.

FIGS. 23A-23B of application Ser. No. 11/124,634, previously incorporated by reference, illustrate a T-tag fastener 2200 with a hydrogel disc 2204 that can be placed between the deployed T-member 2208 and the extragastric (serosal) surface. The disc 2204 could be delivered through the T-tag delivery needle, and unroll after passage through the needle. The hydrogel disc 2204 acts as a buttress or pledget to distribute the forces transmitted between the T-member 2208 and the extragastric surface and thereby it strengthens the attachment of the T-tag fastener 2200. The hydrogel used in FIGS. 23A-23B can optionally be replaced with alternate materials described herein for example silicone, NiTi and fluoropolymers. A Hydrogel or other buttress or Teflon pledget for a T-tag could also deploy in some other manner. The disc configuration shown can be replaced with for example, braided or woven wires or filaments that would expand/deploy after passage through the needle (FIGS. 24A-24B), a Malecot-style deployable tubular structure (FIGS. 25A-25B) or other expandable or deployable configuration (e.g. FIGS. 26A-26B). Although FIGS. 23A-23B, 24A-24B, 25A-25B, and 26A-26B illustrate T-tag fasteners, such as 2200 in FIGS. 23A-23B used with T-members 2208, uses of the T-tag fasteners without T-members and just with the hydrogel disc 2204 of FIGS. 23A-23B or the woven filaments, Malecot-style tubular structure, or the expandable structure of FIGS. 24A-24B, 25A-25B, and 26A-26B, respectively, are also contemplated.

In the above examples where it has been suggested that a fixed distance between the T-member and the device it is being used to attach is desirable it has been suggested that in some cases a distance greater than the thickness of the captured gastric wall may be clinically indicated. This is due to the ability/tendency/possibility that the gastric wall could react to the presence of a foreign body (the attachment structures) by thickening. In this event, in some cases, it can be clinically preferable that the preset distance accommodate some or all of this increase in wall thickness.

The cuff 102 and sleeve 100 may be formed as an integral unit, or supplied to the clinical site as a single unit, for installation as one piece. Alternatively, the cuff 102 and sleeve 100 are provided as separate components, with an instruction that the cuff is inserted first as described elsewhere herein, followed by insertion of the sleeve 100 and attachment of the sleeve 100 to the cuff 102. The sleeve 100 may be attached to the cuff 102 in any of a variety of ways, depending upon the ease with which removal may be desired. For example, stitching or clipping may be accomplished, as described previously. Alternatively, any of a variety of snap fit, interference fit, hooks, loops or other techniques may be utilized.

Figure 13:
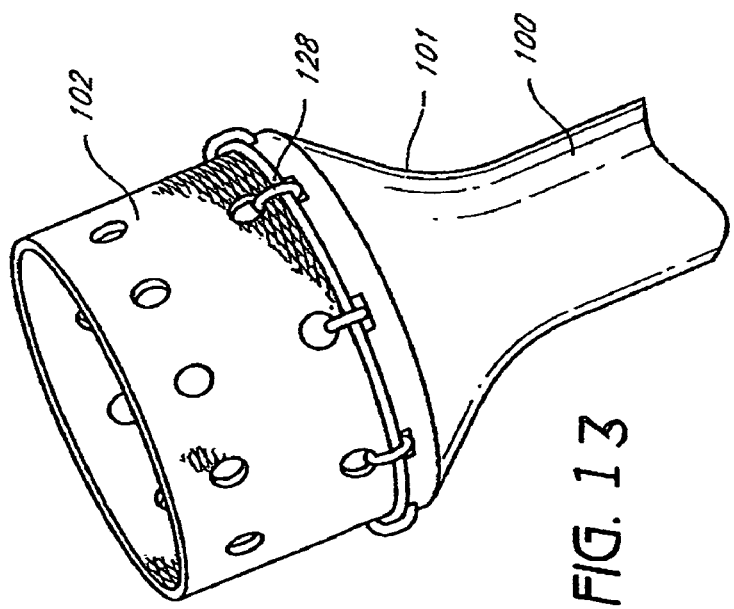
FIG. 13 is a perspective, fragmentary view of a gastrointestinal bypass sleeve connected to an attachment cuff using sutures or clips.

Referring to FIG. 13, there is illustrated a perspective fragmentary view of a device as seen in FIG. 1. In this implementation, a plurality of connectors 128 are provided, for connecting the sleeve 100 to the cuff 102. Connectors 128 are preferably configured for deployment through an endoscope, and may be conventional sutures, or hooks or clips which may be manipulated endoscopically.

Figure 15:
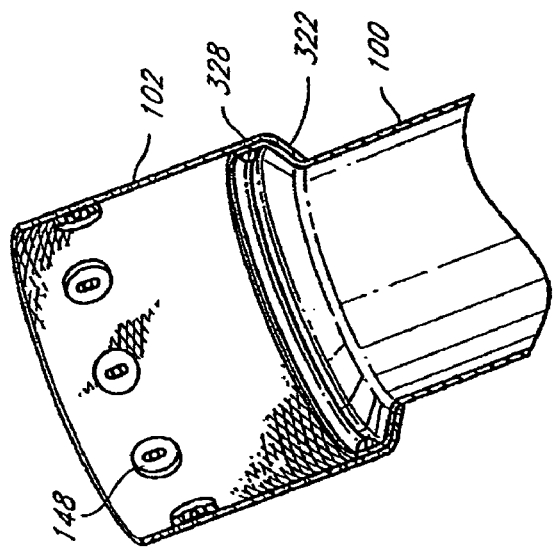
FIG. 15 is a perspective, cross sectional view as in FIG. 14, after the gastrointestinal bypass sleeve has been fully distally advanced into a sealing relationship with the attachment cuff.
Figure 14:
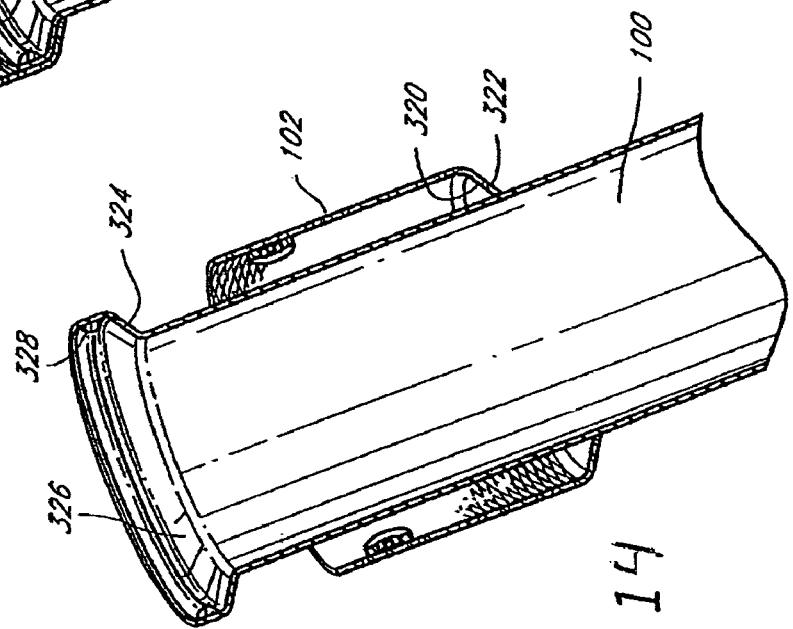
FIG. 14 is a perspective, cross sectional view of a gastrointestinal bypass sleeve being advanced distally through a previously attached cuff.

FIGS. 14 and 15 show two steps in an installation sequence. In FIG. 14, a cuff 102 has been previously attached at a treatment site within the body, such as in the vicinity of the GEJ. The distal end (not shown) of a sleeve 100 has been advanced through the central lumen of the cuff 102, and manipulated down the intestine as disclosed elsewhere herein. The proximal end of the sleeve 102 is provided with an annular radially outwardly extending stop surface as described below. As seen in FIG. 15, the sleeve 100 may be advanced distally until the stop surface on the sleeve engages a corresponding stop surface supported by the cuff 102.

In general, a first retention surface such as an upwardly facing surface 320 on a radially inwardly facing flange 322 or plurality of tabs on the attachment device (cuff) 102 limits distal movement of the sleeve 100 by contacting a second retention surface on the sleeve. The second retention surface may be a downwardly (distally) facing surface 324 such as the distal surface of a radially outwardly facing or inclined annular flange 326 or plurality of tabs on the proximal end of the sleeve 100. In this configuration, the sleeve may be passed through the cuff and simply "dropped" into place and the first and second retention surfaces limit further distal travel of the sleeve relative to the cuff.

Peristalsis and normal gastrointestinal tract activity will place tension or other forces on the sleeve 100. Thus, the connection between the sleeve 100 and the cuff 102 should be sufficient to resist detachment under normal use conditions. For this purpose, the proximal end of the sleeve 100 may be provided with one or more reinforcing structures such as an annular ring 328. A corresponding annular ring or band (not illustrated) may be provided on the radially inwardly facing flange 322. If the outside diameter of the ring 328 exceeds the inside diameter of the ring or other reinforcing structure carried by flange 322, the sleeve cannot be pulled from the cuff 102 unless the force applied is sufficient to deform one or both of the complementary rings. The structural integrity of this type of interfit structure may be optimized, taking into account the likely tension forces applied by the GI system, in view of the desired flexibility and compressibility of the implant as has been discussed.

In other variations of these embodiments, the tubular wall of the cuff can taper inward the distal direction for attaching a sleeve with a smaller diameter than the cuff of the wall the cuff can taper outward in the distal direction for attaching a sleeve with a larger than the cuff.

Each of these embodiments permits the sleeve to be dropped into place or snap fit into place by elastic or other deformation of the interlocking retention surfaces. The attachment can be made more secure by the addition of one or two or more staples, stitches of sutures sdhesives or t-tags. Removal can be accomplished using a removal tool with a stop surface for placing against a surface on the cuff to prevent proximal movement of the cuff, and a grasper for grasping the proximal end of the sleeve and pulling the sleeve to release it from the cuff without straining the connection between the cuff and the tissue. Any additional sutures can be snipped using conventional endoscopic cutting tools. The cuff may also be removed if desired, or a different sleeve may be introduced and secured to the cuff.

The gastrointestinal sleeve device 100 preferably has a length such that ingested food and liquids bypass most or all of the stomach and at least a portion of the small intestine. Undigested food and liquids exit the distal end 112 of the sleeve 100 into the small intestine 114 reducing caloric absorption and eliciting physiological responses within the intestines. See FIG. 1. The gastrointestinal sleeve 100 can have a constant diameter throughout its length or the diameter may vary along the length.

For example, the proximal end of the sleeve 100 may be provided with a diameter that corresponds with the diameter of the cuff 102. This may be in the vicinity of about 25 mm to about 35 mm. The sleeve may be provided with the same diameter throughout its entire length, although this would result in folding of the sleeve longitudinally as it passes through the intestine. For example, the duodenum may have an inside diameter on the order of about 15 mm. As a consequence, one implementation of the invention provides a sleeve having a proximal end having a first cross sectional area, adjacent a tapered or stepped zone across which the cross sectional area reduces to a second, smaller cross sectional area. The axial length of the transition zone may be less than about 2 cm, and some embodiments less than about 5 cm, and in some embodiments no greater than about 10 cm. Alternatively, the length of the transition zone may exceed 10 cm or 20 cm, where wrinkling or longitudinal folding of the sleeve is not sought to be avoided.

The sleeve 100 and cuff 102 may be configured to provide a restrictive opening, either within the sleeve 100 or the cuff 102. The restrictive opening may be effectively provided at the distal end of the transition zone 101 illustrated in FIG. 13. The stoma may be positioned to provide a volume proximally of the stoma of no greater than about 100 cc, and in some implementations of the invention no greater than about 50 cc, and in certain applications no greater than about 30 cc, depending upon the desired clinical result.

As has been discussed in the parent applications previously incorporated herein by reference, additional structures and features may included on the sleeve 100. For example, one or more structures may be provided on the distal end of the sleeve 100 for facilitating transport of the sleeve 100 through the intestinal system. This may include a balloon or other bulking structure to facilitate preferential operation of peristalsis on the distal end of the sleeve. Any such structures may be absorbable, detachable, or permanent, depending upon the desired clinical performance. Alternatively, any of a variety of grasping structures such as a grasping tab or ring may be provided to facilitate grasping the distal end of the sleeve 100 using an installation tool, which is advanced distally through the intestinal system.

The gastrointestinal sleeve 100 can be impermeable along the entire length or some or all of the device may be porous or semipermeable. Preferably, the wall of the gastrointestinal sleeve 100 is thin and flexible so that peristalsis is coupled to the internal lumen of the sleeve 100. A gastric sleeve that extends beyond the pylorus 116, with or without an intestinal sleeve component, can allow use of the pylorus as a natural stoma by configuring the sleeve to close by normal operation of the pylorus 116 and then open to allow passage of food when the muscles of the pylorus relax. The section of the sleeve device 100 that passes through the pylorus 116 will preferably have enough wall flexibility or compliance to allow normal opening and closing of the pylorus to release and retain stomach contents and to allow drainage of stomach secretions around the outside of the sleeve. This can optionally be accomplished by the inclusion of pleats, channels or other structures to facilitate the collapse and sealing of the sleeve as well as passage of gastric secretions along the outside of the sleeve as shown schematically in FIG. 6A.

Dimensions, materials and other specifications described in U.S. patent application Ser. No. 11/124,634 can be selected and adjusted based upon the clinical situation. For example, the gastrointestinal sleeve 100 is preferably approximately 60-180 cm in length whereby partially digested or undigested nutrients exit from the sleeve into the jejunum where they can elicit a hormonal, neural and/or osmotic reaction in the jejunum, ileum and/or duodenum. Increasing the length of the sleeve can reduce the absorption of nutrients in a manner similar to that of a Roux-en-Y or bypass device, as will be understood by those skilled in the art. The sleeve may extend sufficiently far into the intestine, such as past the ligament of Treitz, so that it is retained in the intestine and not pushed back into the stomach. Lengths of at least about 50 cm, at least about 75 cm, at least about 100 cm and at least about 120 cm are contemplated, although different lengths may be appropriate depending upon the requirements of a particular patient. Lengths of no greater than about 5 cm or no greater than about 10 cm or no greater than about 20 cm may be desirable for certain patients, depending upon the desired clinical outcome.

The releasable attachment of the sleeve to the cuff as disclosed herein facilitates removal and replacement of the sleeve 100. Thus, the response of a particular patient to a first sleeve having a first length can be observed. If more or less intestinal absorption is desired, the first sleeve can be endoscopically removed from the cuff, and replaced by a second sleeve having a second shorter or longer length. Therapy is thus adjustable, which may be desirable if either the initial sleeve length was suboptimal or if it becomes suboptimal due to post implantation changes such as stomach remodeling or behavioral changes.

Optionally, the sleeve can include coatings on its interior and/or exterior to enhance the surface properties of the sleeve in clinically relevant manners. Coating examples include: 1) parylene coatings to increase the chemical resistance of a sleeve material, 2) coating with an antimicrobial agent to resist infection and/or 3) coating with an anti-inflammatory agent to reduce tissue inflammatory response, as described herein. Similarly, the interior and exterior of the sleeve can optionally be coated with a low friction material (e.g. a hydrogel) to reduce friction of food passage (interior) and reduce gastric irritation (exterior). One example of such a low friction material is a lubricious coating such as the PHOTOLINK LUBRICIOUS COATING manufactured by Surmodics Inc. and disclosed on pg. 5, paragraph 58, in U.S. utility patent publication 2005-0049718, the disclosure of which is herein incorporated in its entirety by reference.

U.S. patent application Ser. No. 10/698,148 describes the use of biodegradable or bioresorbable materials for construction of a gastrointestinal sleeve device to obviate the need for removal of the sleeve device at the end of the treatment period. The entire gastrointestinal sleeve device or a portion of it may be made of biodegradable material. The gastrointestinal sleeve device may be made of biodegradable materials with different rates of degradation or resorbtion. The gastrointestinal sleeve device may be configured with a series of segments that biodegrade sequentially. For example, a first portion on the distal end of the sleeve may degrade first, followed some time later by a second intermediate portion and a third proximal portion. Next the attachment between the sleeve 100 and cuff 102 would degrade and, finally, the T-tags or other fasteners would degrade. Alternatively, the gastrointestinal sleeve device may be configured with a series of short segments of non-biodegradable material that are attached to one another with biodegradable material. The biodegradable attachment portions may be made of biodegradable materials with different rates of degradation or resorbtion so that they biodegrade sequentially. In either case, the biodegradable material would allow a gradual change of therapy over time, without having to revise or replace the implant. The patient could get used to the gradual change in therapy more readily than a sudden change and may be better able to avoid a rebound in weight gain. It may also allow for a safe mode of degradation and elimination. The device would degrade into pieces small enough that they could be eliminated without any danger of bowel obstruction.

Alternatively, selected portions of the gastrointestinal sleeve device may be made of biodegradable material. For example, openings in the sleeve can be covered with biodegradable material that will gradually degrade over time, eventually allowing food to mix with digestive secretions. The biodegradable material would allow a gradual change of therapy over time, without having to revise or replace the implant. The gastrointestinal sleeve device with the openings in it could be left in place for long-term maintenance of weight loss or it could eventually be removed.

In some embodiments the rate of degradation of the biodegradable material forming the sleeve could be coordinated with the natural pH of the anatomical environment and/or to properties of the material forming the sleeve, to achieve a predetermined sequential degradation of the implant. In accordance with one degradation sequence, a distal (intestinal) portion of the sleeve dissolves before the proximal (gastric) portion. For example, the sleeve could be constructed of a material that degrades at a faster rate in a relatively basic environment than in a relatively acidic environment such that the distal portion of the sleeve in the intestine would dissolve before the proximal portion of the sleeve in the stomach. The pH of the sleeve environment could also be altered by an external source, for example by ingestion of a substance that would change the pH of the stomach and/or intestine and thus hasten degradation of the gastric component. Alternatively, the distal and proximal portions of the sleeve could be constructed of two different materials with the material comprising the distal portion dissolving faster than the material comprising the proximal portion. Alternatively, the material forming the sleeve could be thinner at the distal portion than at the proximal portion such that the distal portion would dissolve in less time than the proximal portion. All or any combination of the above alternatives could be used to set the time frames of degradation of the distal and/or proximal portions of the sleeve depending on the desired performance.

Biodegradable material suitable for construction of a gastrointestinal sleeve device is sold under the name Plastifilm by OsteoBiologics, Inc., located in San Antonio, Tex. This biodegradable polymeric film material is described in U.S. Pat. No. 6,514,286, which is hereby incorporated by reference. Additional information from the supplier about this material is available at: http://www.obi.com/.

Another aspect of the present invention involves devices and methods for delivery and deployment of a gastrointestinal sleeve device into a patient's gastrointestinal tract. One method to facilitate delivery of the device into and through the patient's small intestine is to place a guidewire and/or catheter into the intestine to the depth desired and then push the gastrointestinal sleeve device over the guidewire. Successful techniques for placing a guidewire into the small intestines have been described by G. Long, T. Mills and C. P. Swain in an article entitled *Techniques for advancing guide wires and devices in the lumen of the gastrointestinal tract*. Another technique that could be adapted for placing a device such as a gastrointestinal sleeve device into the small intestine was described by H. Yamamoto and K. Sugano in an article entitled *A new method of enteroscopy—the double-balloon method*, Can J Gastroenterol. April 2003 ;17(4):273-4. These techniques can be used in combination with many of the delivery and deployment methods described herein and in the prior application.

The gastrointestinal bypass sleeve may also be deployed within the intestine using a toposcopic, or everting technique, based upon the method of internal pressurization that is well known in the everting catheter art. Pressurization may be accomplished by placing the proximal end of the axially collapsed sleeve in communication with a source of inflation or everting media, such as a liquid or gas. Liquid such as water or saline may be preferred, and may additionally be provided with a radiopaque additive to permit real time fluoroscopic visualization of the progress of the deployment within the GI system. Additional additives may also be provided, such as antibiotics, nutritional supplements or others as may be desired.

Figure 8A:
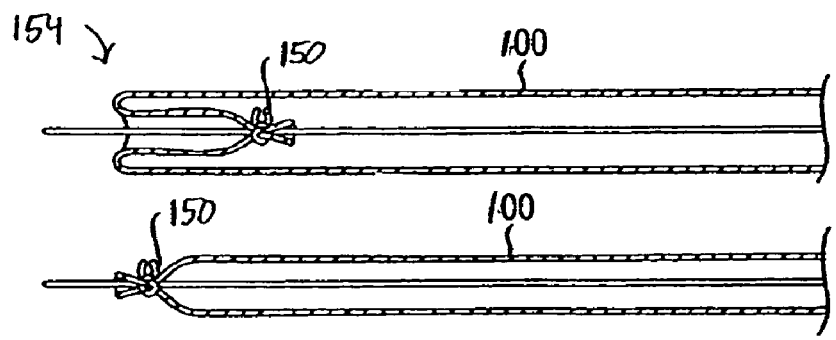
FIG. 8A is a side elevational cross section through a partially inverted sleeve.
Figure 8B:
FIG. 8B is a side elevational cross section through a sleeve, showing an absorbable distal closure.

To maintain the internal fluid pressure used to assist in everting the inverted gastrointestinal sleeve, the distal end of the sleeve may be temporarily occluded or sealed during deployment. FIGS. 8A-8B illustrate one of a number of options for sealing the distal end 112 of a gastrointestinal sleeve 100 during delivery and deployment. FIG. 8A shows the inverted distal end 112 of the gastrointestinal sleeve 100 sealedewith a suture or tie 150 which may be degradable and formulated to dissolve within approximately 2 or 6 or 24 hours in the intestines. Dissolution of the biodegradable tie 150 can be aided by introduction of a solvent, or active agent, or inducing a pH change that is ingested or placed in the everting fluid. The distal end 112 may also be releasably secured to a pull line 152 such as a suture or wire, to assist in inverting the sleeve as will be apparent to those of skill in the art. FIG. 8B shows the noninverted distal end 112 of the gastrointestinal sleeve 100 sealed with a biodegradable tie 150 that may be formulated to dissolve within the intestines, prior to proximal retraction of the pull line 152.

The distal end may alternatively be temporarily occluded using adhesives, such as a water soluble adhesive or pressure sensitive adhesive applied to the interior surface of the distal end 112 of the sleeve. Alternatively, the distal end of the sleeve may be folded over onto itself with or without the use of adhesives. Solvent bonding, thermal spot welding or other bonding technique may be used to close the distal end 112, in a manner that a slight increase in pressure can be applied to the inflation media following full deployment, to rupture the seal. A tie line may alternatively extend proximally from the distal end 112, either inside of the lumen or outside of the sleeve 100. Proximal retraction of the tie line following sleeve placement will untie a knot or otherwise release the distal end 112. Otherwise the distal end may be simply left open during the deployment process.

Figure 9A:
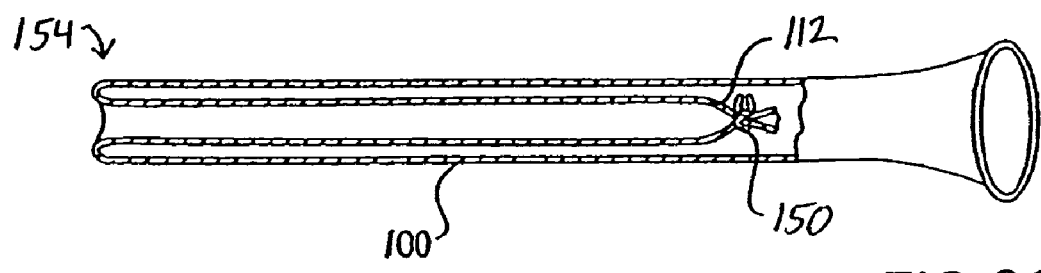
FIG. 9A is a partial cross sectional view of a sleeve having a single invertion.
Figure 9B:
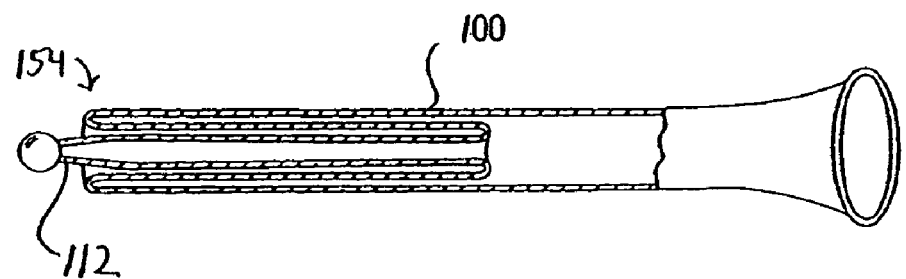
FIG. 9B is a partial cross sectional view of a sleeve having a double invertion.

FIG. 9A shows a gastrointestinal sleeve 100 loaded in an inverted configuration. FIG. 9B shows a gastrointestinal sleeve 100 loaded in a double-inverted configuration. A full single inversion will reduce the length of the sleeve 100 by about 50%, while a full double inversion will reduce the length of the sleeve 100 to about 25% of its original length. Deployment of the sleeve will thus still require a first step of positioning the distal end 154 of the inverted sleeve 100 at a first position within the GI tract, and then second everting the sleeve to position the everted distal end at a second position within the GI tract, downstream from the first position. The second position will normally be at least about 50 cm and often at least about 75 cm or 100 cm distally of the Pyloris. The first position may be at about the Pyloris, within about 20 cm of the Pyloris, or within about 50 cm of the pyloris, depending upon the device design and desired deployment procedure.

Inverting the sleeve simplifies the delivery and deployment of the device, but it adds some additional constraints to the configuration of the device. The inverting segments can have very thin walls and inverting interfaces can be highly lubricious for easy and reliable deployment. For example blow molded 90A durometer polyurethane of a wall thickness on the order of 0.005"or less, most preferably about 0.002", with a lubricious coating will work in this manner. Eversion within the intestine may be accompanied by introduction of an irrigating or lubricating fluid on the outside of the sleeve 100, and/or provision of a lubricant in between contacting surfaces of the inverted sleeve. Additional details are disclosed in copending application Ser. No. 10/698,148, filed Oct. 31, 2003, entitled Apparatus and Methods for Treatment of Morbid Obesity, the disclosure of which is incorporated in its entirety herein by reference.

Methods of insertion and retrieval of a gastrointestinal sleeve device are also described in the parent application. In addition to the methods described therein, a GI sleeve can be inserted and/or retrieved using a flexible endoscope. A skilled GI endoscopist can "drive" a special endoscope (an enteroscope) through the duodenum and deep into the jejunum. Because of its small size, a pediatric colonoscope can be used to access an area further down the intestine. With proper interfacing structure on a GI sleeve, the sleeve can piggyback on the endoscope as it is driven into the jejunum and then released with its distal end left in the jejunum when the endoscope is retracted and removed from the body. This can be accomplished perorally either before or after attachment of the proximal end of the sleeve to tissue or to a cuff at the GEJ or some other clinically desirable location.

Various structures can be used as an interface between the endoscope and the distal end of the GI sleeve device. If the sleeve device has a solid distal end or other graspable portion, such as a tab or loop near the distal end, a standard or custom endoscopic snare or grasper can be extended through the endoscope working channel to grasp the sleeve device. Alternatively, the distal end of the sleeve device can be configured with a socket or pocket to engage a flexible pusher, which may be configured as a rod, tube or guidewire. As another alternative, the sleeve device can be configured with a distal end that can be cut off to release the device. The distal end of the sleeve device is grasped with a snare or the like extended through the endoscope working channel. Once the sleeve device is delivered far enough distally in the GI tract, the distal end of the sleeve device is cut off to release the device.

In one embodiment, delivery of the sleeve device to an area sufficiently far down the intestine is facilitated by attaching a traction structure, such as a mercury ball or liquid filled balloon, that increases the likelihood that the sleeve will be pulled down the intestine, to the distal end of the sleeve. During peristalsis the intestinal wall grabs hold of the traction structure and pulls it along with the distal end of the sleeve down the intestine.

In one embodiment deployment of the sleeve device and/or T-tags is achieved with the use of a remote controlled robotic endoscope. Generally, a remote controlled robotic endoscope comprises a user interface, a control device, and an operating unit. Commands can be inputted by an operator into the user interface to activate the control device which in turn guides the operating unit in three dimensions. The operating unit, in one embodiment, can be a fastener deployment head carried by a catheter which is positionable within the gastrointestinal tract and capable of attaching various fastener structures such as sutures and T-tags in response to commands received by the user interface. Monitors that display physical data and images of the anatomy to aid in navigation of the operating unit may also be used with a remote controlled robotic endoscope. Such an endoscope could scale the operator's movements such that large movements of the operator would translate into the smaller movements that may be required to maneuver the endoscope within the gastrointestinal tract. One embodiment of a remote controlled robotic endoscope is described in "Radiocontrolled Movement of a Robot Endoscope in the Human Gastrointestinal Tract," by P. Swain, T. Mills, B. Kelleher, L. Schmitz, S. Mosse, P. Burke, K. Ikeda, and A. Fritscher-Ravens.

Figure 10:
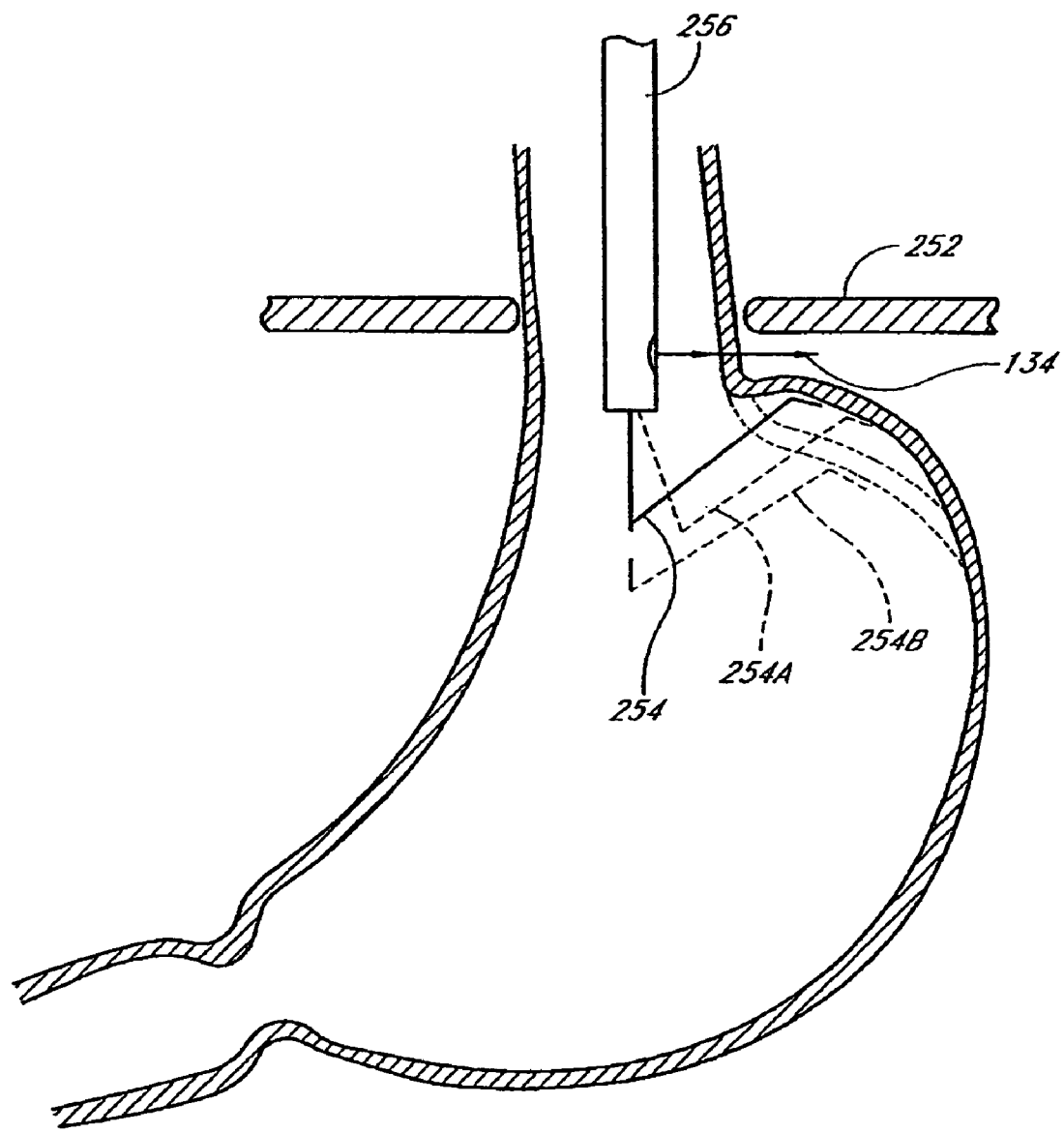
FIG. 10 illustrates a method and apparatus for placing T-tag fasteners at the gastroesophageal junction (GEJ).
Figure 11A:
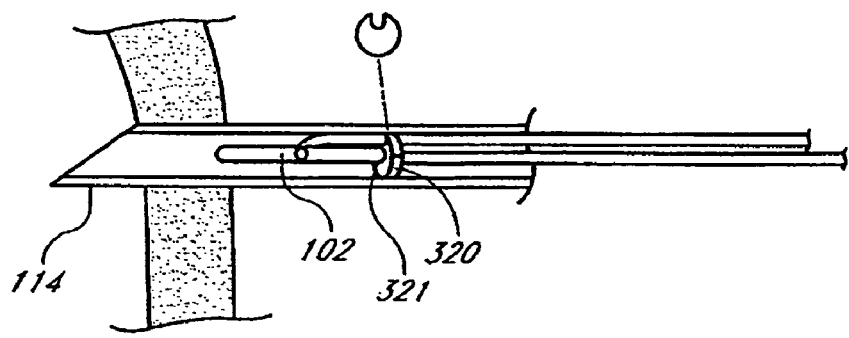
FIGS. 11A-11D show a method of T-tag fastener delivery.
Figure 11B:
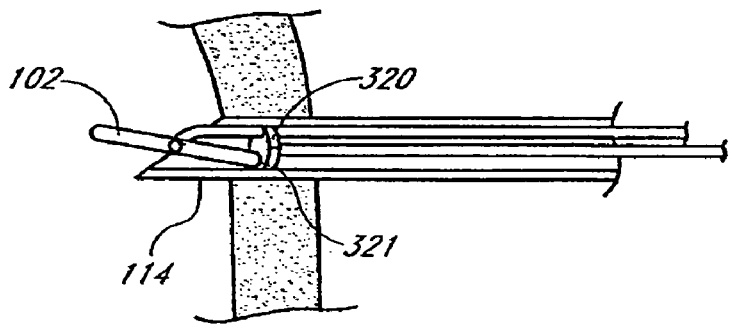
Figure 11C:
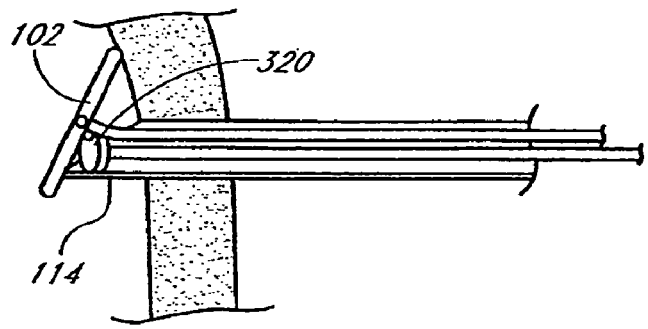
Figure 11D:
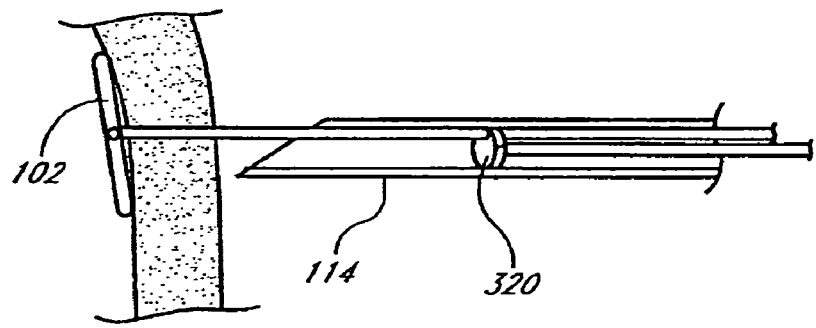

When placing T-tag fasteners or other fasteners in the region of the GEJ, it is important to avoid other anatomical structures in the vicinity of the stomach and esophagus. One method for this is to create a safe space behind the GEJ for deploying the fasteners. One method to accomplish this is described in the parent application Ser. No. 10/698,148. Alternatively, one can take advantage of the fact that the proximal stomach generally lies just below the diaphragm when the patient is in a head-up position. Space will be created between the stomach and diaphragm into which transmural fasteners can be safely placed. This safe space can be increased by having the patient inhale deeply while in a head-up position to push the stomach down with the diaphragm, then exhale to lift the diaphragm up off of the stomach. Preferably, the fasteners 134 will be delivered parallel to the diaphragm 252, as shown in FIG. 10, though other orientations are possible. FIG. 10 also shows an optional stomach traction device 254 deployed through the working channel of an endoscope 256 that helps to facilitate safe deployment of the fasteners 134 in the GEJ region. The traction device 254 can be used to retract the gastric wall laterally 254A and/or distally 254B to create a safe place for deployment of the fasteners 134. Due to anatomic variations and pathology, the position of the diaphragm relative to the stomach and GEJ should be confirmed prior to using this technique.

Alternatively or in addition, pneumoperitoneum can be used to create a safe space around the stomach and esophagus. Pneumoperitoneal pressure will tend to collapse the stomach away from other surrounding organs and would be balanced by the pressure used to endoscopically insufflate the stomach for improved visualization and access.

Other tactics to avoid other anatomical structures in the vicinity of the stomach and esophagus include the use of imaging techniques such as fluoroscopy, esophageal ultrasound imaging, external ultrasound imaging and/or Doppler imaging when placing fasteners. Alternatively or in addition an "endoscopic compass" can be used to provide a reference for orienting the endoscope when using fastening devices. A small magnetized needle (i.e. a compass needle) is placed near the distal end of the endoscope where it can be viewed by the operator through the endoscope. A magnet is placed on the patient to provide a reference point for the compass, for example the reference magnet can be placed on the patient's back directly over the spine. The compass needle will point toward the reference magnet on the spine. Using the compass needle as a reference, the operator will be able to avoid inadvertently puncturing the aorta, which lies directly posterior to the esophagus.

The concept of the Veress needle can be adapted for avoiding puncturing other anatomical structures in the vicinity of the stomach and esophagus during endoscopic attachment of devices near the GEJ. A Veress needle is a needle equipped with a spring-loaded obturator that is often used for insufflation of the abdomen in laparoscopic surgery. A long, flexible device with a needle at the distal end and a spring-loaded obturator within the needle would be used to safely puncture the gastric or esophageal wall. Once the needle has passed through the wall, the spring-loaded obturator advances automatically to avoid damage to any surrounding tissues. A delivery cannula can be advanced over the needle and the needle can be exchanged with a fastener delivery device. Alternatively, this concept can be adapted directly into the fastener delivery device. A T-tag fastener or the like would be spring-loaded into the lumen of a delivery cannula so that it would be ejected out of the lumen immediately after the cannula has traversed the gastric or esophageal wall.

Another method for avoiding deploying fasteners into the aorta would involve a small diameter needle with a flow detector (e.g. a Doppler flow sensor) or pressure detector for detecting blood flow or blood pressure. Alternatively, a flow detector or pressure detector can be mounted on a separate guidewire inserted through the needle. The flow detector can be used to detect blood flow before the wall of the aorta is punctured. Alternatively, if backflow of blood or blood pressure is detected, indicating that the needle has punctured the aorta, the needle will be withdrawn and a fastener will not be delivered at that site. The small diameter puncture in the aorta should heal without complications.

Alternatively or in addition, the organs and other anatomical structures in the vicinity of the stomach and esophagus can be protected during endoscopic attachment techniques by using a depth stop on the needle or delivery cannula to prevent it from penetrating farther than necessary to traverse the gastric or esophageal wall. Examples of fastener delivery devices with a depth stop to protect nearby organs and structures are described in U.S. provisional patent application 60/569,442.

FIGS. 11A-11D illustrate a simplified view of delivery of a T-tag fastener showing the serosal anchor and tension element (suture) of a T-tag fastener and the delivery cannula with a pusher therein. In actual application, the entire delivery assembly would include an endoscopic delivery device (not shown), with the delivery cannula carried piggyback by the endoscope or deployed through the working channel of the endoscopic delivery channel. Also, in actual application the T-tag fastener would attach an attachment device such as a cuff to a gastrointestinal sleeve device through a grommet or hole in the cuff and/or sleeve device.

All or a portion of the fastener can be coated and/or made with a material that will encourage tissue ingrowth to create a seal and to promote a strong and durable attachment, although tissue ingrowth in the vicinity of the GEJ is not expected to be robust. All or a portion of the fastener can be coated and/or made with a swellable material to create a seal and/or to spread out the force of attachment over a greater surface area, thereby reducing the pressure on the tissue. All or a portion of the fastener can be coated and/or made with a material that is biodegradable or bioresorbable. Examples of such coatings materials are described in the parent application Ser. No. 10/698,148.

One method for placing an implantable device within a patient's body has been described as a "parachuting" technique. In this technique, multiple elongated sutures extend from a plurality of implanted serosal anchors where the device is to be implanted with the ends of the sutures extending out of the patient's body. The ends of the sutures are passed through a sewing ring or similar structure on the device while the device is still outside of the patient's body, then the cuff is parachuted or slid into place along the sutures. The cuff is typically secured in place by knotting the elongated sutures with the help of a knot pusher or similar device and then the sutures are cut off close to the knots. U.S. provisional patent application 60/534,056 describes a variation of this method for implanting a device within a patient's digestive tract using T-tag fasteners. Alternatively, suture locks such as those described in U.S. Pat. No. 4,235,238, the disclosure of which is hereby incorporated in its entirety by reference herein, or those used in the BARD Endocinch system can be used to secure the suture prior to cutting.

When parachuted into place along the sutures, the cuff may be folded or compressed to pass through the esophagus or through a delivery tube placed in the esophagus. When using this parachuting technique it is desirable to minimize the friction between the device and the sutures. This can be done by using a low friction material or a low friction coating on the sutures and/or the device. This is also done by dimensioning and/or orienting structures, e.g. holes, to guide the parachuted device to reduce friction.

Figure 12:
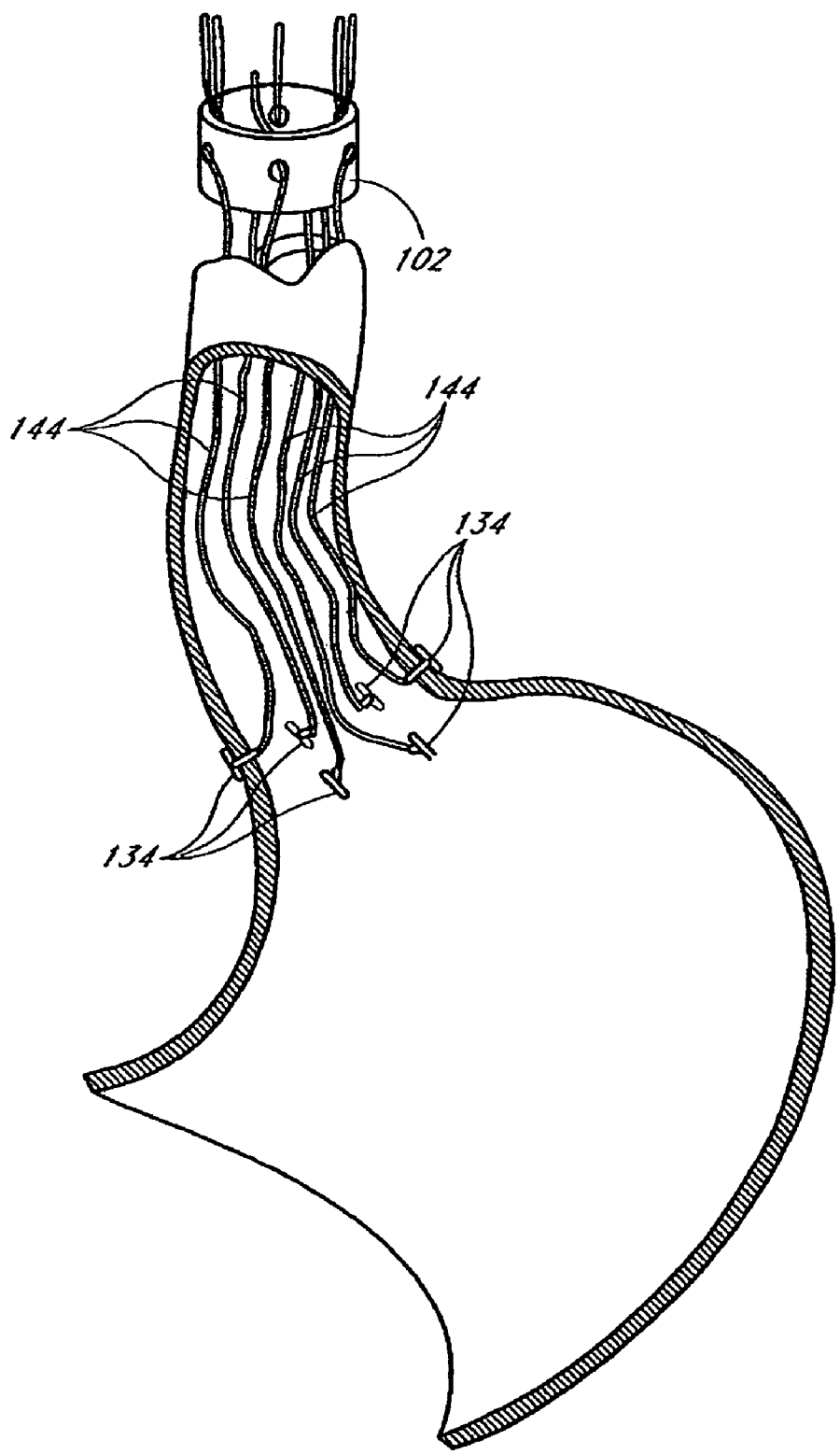
FIG. 12 shows a cuff being parachuted into place along a plurality of suture tails.

FIG. 12 shows an implantable device 102 being implanted at the GEJ using a parachuting technique. One method of using a fastener delivery device for placement of an implantable device 102 by the parachuting technique is disclosed in U.S. utility patent application Ser. No. 11/025,364, previously incorporated by reference herein.

Alternatively, the device 102 may be partially parachuted into place, meaning that 2-4 parachute sutures are used to slide the device 102 into position with the proper orientation. Then additional fasteners, for example T-tag fasteners, are delivered endoscopically to complete the attachment of the device 120 to the tissue.

If suture tails are delivered through a closed lumen (e.g. in or attached to an endoscope), the lumen must be removed from around the suture tails before a device can be parachuted over the sutures if the device is too large to pass through the lumen. This can present a challenge related to maintaining the organization of the suture tails and preventing confusion, crossing, winding and/or tangling of the suture tails. If T-tag fasteners and their suture tails are passed externally e.g. through an external lumen with a longitudinal slot or in a non-enclosed rail type system, the suture tails can be managed external to the lumen used to place the T-tag fasteners and external to the scope. This facilitates manipulation of the scope, simplifies scope exchanges and simplifies suture tail management.

Suture tail management external to the scope or an enclosed lumen can be combined with suture holders external to the patient, similar to those used for parachuting replacement heart valves into place. Snugging the sutures as described above is simpler when the suture tails are external to the scope, as is avoidance of crossing, winding and/or tangling of the suture tails. Suture holders, such as slots, clamps or clips, can be combined with a mouth guard for organizing the sutures during a peroral parachuting procedure.

One aspect of suture tail management is that it must happen from one end of the system to the other. Therefore, the method and apparatus must address this issue. For example, after placement of a T-tag fastener, a slight tension on the suture tail can hold the suture against the wall of the lumen or in a straight position where it is less likely to tangle. Apparatus can include means to maintain tension while allowing scope movement and manipulation, e.g. tension from a long soft spring, an elastic band or a spring-loaded reel.

Sometimes, when performing an endoscopic procedure, an overtube is used to line the esophagus and protect it from damage due to insertion and manipulation of the endoscope and related tools and devices. Other practitioners prefer to avoid the use of an overtube. In either case, it may be desirable to secure an implant being parachuted down the esophagus in a collapsed, folded or otherwise reduced configuration. A major issue when parachuting a device into place is friction between the device and the sutures, and collapsing or folding the device may exacerbate the problems with friction.

The following method is intended to reduce the problems with friction between the device and the sutures when parachuting a device through the esophagus. The method allows the device to be parachuted through the esophagus in a folded configuration, while it also allows the sutures to pass through the device while it is in an unfolded position. In addition, the method allows the sutures to be pulled through the device one at a time, which further reduces the problems with friction. This method can be used, for example, with the t-tag and/or t-tag delivery systems described herein.

1) Place fasteners (e.g. 6-10) in or through gastric wall with suture tails extending out through the patient's mouth; the sutures should have a length that is about 100-140 cm longer than required to exit the mouth;

2) thread suture tails through the device to be parachuted into place, e.g. an implant mounting ring or cuff;

3) slide the cuff down the sutures until it is just outside of the patient's mouth, with 100-140 cm of suture extending beyond the device;

4) fold or collapse the cuff and secure it in the collapsed position, e.g. with a removable sack or tied with a suture;

5) slide the cuff through the esophagus or the scope overtube (the cuff is not slid down the sutures, but instead the sutures are allowed to move with the cuff into the esophagus with the ends of the sutures remaining outside the patient);

6) once the cuff is through the esophagus and at the deployment site, the cuff is released from its collapsed position, and any restraining device that was used is removed perorally;

7) while controlling the cuff (e.g. with a grasper), and preferably under direct vision, pull each suture through the cuff until all the slack is removed and the cuff is at or near its intended position in the stomach;

8) position and secure the cuff in its intended position in the stomach.

In some clinical situations the gastroesophageal junction, or GEJ, is a preferred attachment point for a gastroesophageal sleeve device or attachment device as discussed above. Attachment at the GEJ excludes all gastric secretions from the interior of the gastrointestinal sleeve device to separate ingested food and liquids in the sleeve device from all digestive secretions. The gastroesophageal junction is one of the preferred attachment sites because the tissue wall is relatively thick at this location and it is relatively easy to access via a peroral route. More specifically, the non-glandular tissue directly above the squamo-columnar junction (a zone of tissue that is considered to be at the beginning of the GEJ) is the strongest tissue in this region and is currently thought to be the best place to attach a device, for example using T-tags, sutures or other fasteners.

In some clinical situations it may be beneficial to pre-strengthen the tissue prior to implantation of a device such as a gastrointestinal sleeve device. For example, energy can be delivered in the form of RF, ultrasound or other known method to induce an inflammatory, coagulative or necrotic tissue strengthening reaction. Alternatively, placement of material in the serosal tissue of the stomach wall could generate a foreign body reaction that would progress from inflammation, to granulation of tissue and then to fibrosis. The tissue may initially weaken due to the inflammatory response, but the resulting fibrotic growth will strengthen the tissue. This effect could be enhanced by the choice of material an/or coatings, e.g. sclerosing agent, an acidic material or coating. The materials could be delivered endoscopically with a needle device through the biopsy channel of an endoscope. The needle delivery device could optionally also deliver an ink, dye or other marking means to facilitate location of the prestrengthened areas. Tissue reaction could take place in days, with 7-14 days being an approximate delay between prestrengthening and attachment procedures.

Material injectable to prestrengthen tissue could be: 1) liquid where natural processes would remove/break down or otherwise dispose of the liquid when it has complete its function; 2) biodegradable or dissolvable where natural processes would remove the material when it has completed its function; or 3) permanent where the material might be incorporated into the tissue to provide increased strength. All of the prestrenghening strategies described could be used at the time of the attachment procedure to enhance strenght of the attachment.

The methods and apparatus described for tissue strengthening would be expected to result in some degree of tissue thickening as new collagen and fibrotic material will be deposited and/or generated at the location of the foreign body reaction. The duration of exposure can be controlled by use of timed release chemical stimulants and stimulants with known and potentially controllable half lives. Tissue thickening and tissue strength may be related and may facilitate durable attachment, however tissue thickening may be an inherently desirable result in some clinical situations.

Currently, tissue bulking agents are injected at or near the GEJ to treat GERD. Injection of non-bulking materials that initiate tissue thickening could accomplish the same result. If the thickened tissue was, by itself or in conjunction with a supporting structure, to form a restrictive stoma, there could be specific advantages relative to a mechanical stroma.

Other approaches to induce tissue prestrengthening and/or thickening include: Circumferential ablation (RF, microwave, ultrasound, etc); Over-dilation; Circumferential abrasion; and, Circumferential exposure to agent. An advantage of a continuous or segmented circumferential area of tissue strengthening is that it only needs to be located along a vertical axis for subsequent attachment procedures.

Alternately or in addition to the above pre-strengthening of tissue, tissue can be treated to reduce its ability to move or stretch. This can be advantageous in that tissue that has limited stretch or motion may have less impediments to attachment. Tissue that has limited stretch or motion may impose fewer forces on an attached device and therefore impose less force or pressure that may lead to attachment failure. Furthermore, tissue that has limited stretch or motion may allow attachment of less compliant devices which can provide for advantages foe example simplified sealing.

Techniques described above to strengthen tissue can also help to limited GI tissue stretch and motion. Other methods that could be applied to reducing stretch and motion, and also for pre-strengthening, include the application of energy for example, by RF, ultrasound or laser. Means that include time release elements as well known in the art of drug eluting vascular stents and birth control devices can be used to provide and/or maintain a long lasting effect (reducing motion and stretch). Such time release means can optionally be combined with fasteners, permanent or replaceable attachment cuffs or proximal sleeve interfaces. Such time release means can optionally be combined with permanently implanted pre-strengthening materials where the material might be incorporated into the tissue to provide increased strength.

In some clinical situations when using a transmural attachment, the wall of tissue may thicken after placement of the attaching device. In some cases this can progress to encapsulation. This thickening can result in increased tissue strength due to collagen deposition and/or fibrosis.

In some clinical situations it can be advantageous to maintain the attachment on the surface of the tissue to take advantage of the added strength of the thickened wall. This may be accomplished by permitting controlled suture lengthening to compensate for tissue thickening. One manner in which this could be accomplished would be by using a suture connecting the attachments on either side of the tissue wall that would stretch as the tissue thickens.

One configuration of material that could have advantageous performance would: 1) not stretch for an initial period, for example 24-48 hours; 2) stretch at a relatively low force for the next period, for example 7-14 days; then 3) not stretch after the second period. This performance would be based upon a clinical situation where tissue proliferation (wall thickening) occurs between days 2 and 14. Alternatively, the material could: 1) not stretch for the initial period, for example 24-48 hours; 2) allow lengthening to 2× length at any time after the initial period, for example 48 hours; then 3) not stretch beyond 2× length.

The length of the suture or other tension element which extends through the wall from the serosal surface to the mucosal surface, particularly when the tension element has a substantially fixed length under normal use conditions may also be important. The present inventors believe that the length of the tension element is in certain applications at least about 75%, often at least about 100%, and preferably at least about 120% and possibly at least about 130% of the thickness of the wall of the stomach through which the tension element is to be placed. Thus, for a patient having a wall thickness in the vicinity of the gastroesophageal junction of approximately 10-15 mm, suture lengths between the mucosal contacting surface of the implant and the serosal contacting surface of the retention element of at least about 10 mm, and often at least about 15 mm are contemplated.

The stomach appears to have unusual abilities to isolate foreign objects. Evidence of this is the lap band which can migrate from the serosal surface of the stomach into the lumen of the stomach without any immediate catastrophic event such as a leak of stomach contents into the body cavity which could be life threatening. The cause of such erosion is unclear but one theory suggests it is at least in part due to pressure.

The stomach is also a very active organ with an ability to stretch, compress, churn and move laterally relative to itself. This activity is normal in eating and digestion and can also function to isolate foreign objects.

These anatomical aspects make attachment of medical devices to the stomach quite challenging. A recent study at the Cleveland Clinic which sutured a prosthetic cuff to the GEJ showed that by 7 days 80% of the cuffs had become primarily detached. In one animal that was survived for two months, the device remained attached at 4 weeks but was only 25% attached by 60 days.

The present inventors have conducted a series of studies to explore the parameters of a successful attachment. Initial designs utilizing rigid rings lost attachment at a majority of points within four weeks. Short term success at two weeks with a flexible cuff, with elastic ability, was achieved by using t-tags and placing them in the non-glandular tissue region of the GEJ. However this same technique at five weeks did not maintain 100% attachment. One-Third of the attachment points migrated through the stomach, leaving no identified histological evidence of their path. The t-tags did not appear to be deformed.

The inventors then undertook a series of experiments at five weeks controlling for the amount of tension on the tension element, by placing serosal surface attachment devices having tension elements with a predetermined length relative to the thickness of the tissue wall. The thickness of the porcine stomach at the target site was measured, and the average of four tissue thickness measurements at the 3-6-9-12 o'clock positions was used as the nominal thickness. The absolute thickness was somewhat surprising at around 1 cm. This was perceived to be much thicker than what was thought. The reasons for this could be increased thickness in the area of interest of the GEJ, but it could also be due to the highly compressible nature of stomach tissue in that when it is held between the thumb and index finger it does feel 1 cm thick.

In three experiments conducted there was a clear trend that the looser the attachment (i.e., the longer the length of the tension element compared to the local wall thickness) the more attachment points held at five weeks. Results ranged from 10/12 migrations for the sutures sized at 50% of nominal thickness to 2/12 migrations for sutures sized at 100% of nominal thickness.

Another variable which was explored in the porcine model was the effect of changes in the surface area of the retention element. Silicone buttons having a 1 cm diameter were used instead of the t-tags. In one experiment conducted to date at a suture length of 75% of nominal thickness, 4/12 silicone buttons migrated through.

What seemed different about the silicone buttons is with two-thirds of the attachments in place it appeared upon gross inspection to be very strongly functionally attached, with high weight bearing abilities, perceptually greater than the t-tags.

From the experiments to date it appears that tension control is as important (if not more so) as the geometry of the serosal attachment device.

As discussed elsewhere herein, tension control could be addressed by using suture with limited elastic properties or other structural mechanism that would stretch or elongate and then return to their nominal length. Another way is to use an assumed thickness, based upon an average of actual measurements in humans, and preset the length of the tension element at a predetermined length (e.g., at least 115%, at least 130%) compared to the length of the average. The chances of success for this approach would likely be enhanced if the patient to patient variation is relatively small. A further approach would be to measure the thickness of the target tissue in each patient, and customize the length of the tension element at the clinical site, or provide kits with a cuff and an array of anchor assemblies with tension elements of different predetermined lengths from which the clinician can make a selection. Measurement could be accomplished, for example, with endoscopic ultrasound, like a device available from Boston Scientific.

Once the measurement is taken a variety of devices could be used to attach with a controlled length. Many of these devices have been previously described and include t-tags, inflatable silicone discs, molly type devices, radial spoke "umbrella" structures and others. They can be attached to suture with a fixed cuff to retention element length (or other means) or a strut member made of polymer or metal with a nub to fix the length. All of these devices are preferably configured to permit endoscopic delivery through a single fire device, or a multiple fire or rapid reloadable device could be used, to minimize the number of times the delivery device needs to removed from the endoscope to be reloaded.

Another application of the present invention involves the placement of a mounting ring, aperture, hook, connector or other attachment device within the gastrointestinal system utilizing the serosal attachment disclosed herein and attaching any of a variety of devices or components to the attachment device. Applications for treating GERD, MO and other disorders of the gastrointestinal tract include placing/attaching a nonrestrictive mounting ring at or near the GEJ and attaching/removing/replacing various therapeutic or diagnostic devices to the mounting ring, such as a valve to prevent reflux, a restriction to food intake, a sleeve, a telemetry or imaging capsule, transmitters for transmitting pH or other data, receivers for receiving therapeutic signals initiated by an external control, etc.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. A gastrointestinal implant system, for providing an endolumenal bypass from a patient's gastroesophageal junction to the patient's intestine, comprising:
    a flexible, tubular attachment cuff, having a proximal end and a distal end;
    a first plurality of apertures in the proximal end of the tubular attachment cuff, for receiving tissue anchor tension elements;
    an elongate, flexible bypass sleeve, separate from the cuff;
    a first attachment structure on the distal end of the attachment cuff, for attaching the cuff to the bypass sleeve;

a second attachment structure on the proximal end of the bypass sleeve, for cooperating with the first attachment structure to attach the cuff to the sleeve; wherein the first attachment structure on the attachment cuff is configured to removably attach the cuff to the bypass sleeve; and an everting tool, configured to transform the bypass sleeve from a first, at least partially inverted configuration to a second everted configuration.

2. The gastrointestinal implant system of claim 1, wherein the sleeve comprises a length of at least about 50 cm.

3. The gastrointestinal implant system of claim 1, further comprising a reinforcement element configured to distribute the force of at least one of the anchor tension elements across a surface area.

4. The gastrointestinal implant system of claim 3, wherein the reinforcement element comprises a T-tag.

5. The gastrointestinal implant system of claim 1, wherein the first attachment structure comprises a first retention surface, and the second attachment structure comprises a second retention surface, the first retention surface configured to engage with the second retention surface to limit movement of a proximal end of the sleeve relative to the cuff when a distal end of the sleeve is advanced through a central lumen of the cuff.

6. The gastrointestinal implant system of claim 1, wherein the first attachment structure comprises a flange configured to engage with the second attachment structure.

7. The gastrointestinal implant system of claim 1, wherein at least one of the first attachment structure or the second attachment structure comprises a second plurality of apertures extending through a wall of said attachment cuff or tubular sleeve.

8. The gastrointestinal implant system of claim 1, wherein at least one of the first attachment structure or the second attachment structure comprises a plurality of connectors for attaching the cuff to the bypass sleeve.

9. The gastrointestinal implant system of claim 8, wherein at least one of the plurality of connectors is selected from the group consisting of: a suture, hook, and a clip.

10. The gastrointestinal implant system of claim 1, wherein the first attachment structure comprises an annular ring.

11. The gastrointestinal implant system of claim 1, wherein the first attachment structure and the second attachment structure are configured to allow the sleeve to be removed from the cuff while the attachment cuff is attached within a gastrointestinal tract of a patient.

12. The gastrointestinal implant system of claim 1, wherein the everting tool comprises a source of everting media.

13. The gastrointestinal implant system of claim 12, wherein the everting media comprises a source of liquid everting media.

\* \* \* \* \*